(12) United States Patent
Lett et al.

(10) Patent No.: US 8,290,236 B2
(45) Date of Patent: Oct. 16, 2012

(54) QUANTITATIVE, MULTISPECTRAL IMAGE ANALYSIS OF TISSUE SPECIMENS STAINED WITH QUANTUM DOTS

(75) Inventors: G. Scott Lett, Hightstown, NJ (US); Ned C. Haubein, Yardley, PA (US); Gary Pestano, Lafayette, CO (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/134,303

(22) Filed: Jun. 3, 2011

(65) Prior Publication Data

US 2011/0235880 A1 Sep. 29, 2011

Related U.S. Application Data

(62) Division of application No. 11/999,914, filed on Dec. 6, 2007.

(60) Provisional application No. 60/876,493, filed on Dec. 20, 2006.

(51) Int. Cl.
*G06K 9/00* (2006.01)

(52) U.S. Cl. .................... 382/133; 382/128; 382/129

(58) Field of Classification Search .................. None
See application file for complete search history.

(56) References Cited

U.S. PATENT DOCUMENTS

| | | | |
|---|---|---|---|
| 4,786,813 A | 11/1988 | Svanberg et al. | 250/461.1 |
| 5,018,209 A | 5/1991 | Bacus | 382/129 |
| 5,428,690 A | 6/1995 | Bacus et al. | 382/128 |
| 5,798,262 A | 8/1998 | Garini et al. | 435/287.2 |
| 5,926,283 A | 7/1999 | Hopkins | 356/419 |
| 5,990,479 A | 11/1999 | Weiss et al. | 250/307 |
| 6,007,996 A | 12/1999 | McNamara et al. | 435/6 |

(Continued)

FOREIGN PATENT DOCUMENTS

WO WO 97/22848 6/1997

(Continued)

OTHER PUBLICATIONS

US 7,099,500, 08-2006, McLaren et al. (withdrawn).

(Continued)

*Primary Examiner* — Ton Y Lu
*Assistant Examiner* — Thomas Conway
(74) *Attorney, Agent, or Firm* — McDonnell Boehnen Hulbert & Berghoff LLP

(57) ABSTRACT

A biological sample such as a tissue section is stained with one or more quantum dots and possibly other fluorophores (total number of fluorophores N). A camera coupled to a microscope generates an image of the specimen at a plurality of different wavelengths within the emission spectral band of the N fluorophores. An analysis module calculates coefficients $C_1 \ldots C_N$ at each pixel from the set of images and reference spectral data for the N fluorophores. The coefficients $C_1 \ldots C_N$ are related to the concentration of each of the individual fluorophores at each pixel location. Morphological processing instructions find biological structures, e.g., cells, cellular components, genes, etc., in the images of the specimen. Quantitative analysis is performed on the identified biological structures. A display module displays the quantitative analysis results to the user, along with images of the specimen. The images can include images constructed from one or more of the coefficients $C_1 \ldots C_N$. The quantitative analysis display includes histograms of the biological structures, scatter plots of fluorophore concentrations, statistical data, spectral data and still others.

23 Claims, 15 Drawing Sheets

U.S. PATENT DOCUMENTS

| | | | | |
|---|---|---|---|---|
| 6,055,325 | A | * | 4/2000 | Garini et al. ................. 382/129 |
| 6,165,734 | A | | 12/2000 | Garini et al. ................. 435/7.21 |
| 6,215,892 | B1 | | 4/2001 | Douglass et al. ............ 382/128 |
| 6,274,323 | B1 | | 8/2001 | Bruchez et al. ................... 435/6 |
| 6,322,901 | B1 | | 11/2001 | Bawendi et al. ............. 428/548 |
| 6,403,947 | B1 | | 6/2002 | Hoyt et al. .................... 250/226 |
| 6,404,906 | B2 | | 6/2002 | Bacus et al. ................. 382/128 |
| 7,009,699 | B2 | | 3/2006 | Wolleschensky et al. .... 356/317 |
| 7,072,770 | B1 | | 7/2006 | Schweitzer et al. ............ 702/25 |
| 7,146,372 | B2 | | 12/2006 | Bacus et al. ................. 707/100 |
| 7,149,332 | B2 | | 12/2006 | Bacus et al. ................. 382/128 |
| 7,426,026 | B2 | * | 9/2008 | Matsumoto et al. ......... 356/317 |
| 7,555,155 | B2 | * | 6/2009 | Levenson et al. ............ 382/133 |
| 7,689,023 | B2 | | 3/2010 | Rabinovich .................. 382/133 |
| 2001/0033364 | A1 | | 10/2001 | Cabib et al. .................. 351/221 |
| 2001/0033374 | A1 | | 10/2001 | Hoyt ............................ 356/317 |
| 2002/0001080 | A1 | | 1/2002 | Miller et al. ................. 356/326 |
| 2003/0151741 | A1 | | 8/2003 | Wolleschensky et al. .... 356/317 |
| 2004/0042659 | A1 | | 3/2004 | Guo et al. ..................... 382/176 |
| 2004/0066960 | A1 | * | 4/2004 | McLaren et al. ............. 382/128 |
| 2004/0101210 | A1 | | 5/2004 | Weinstein et al. ........... 382/284 |
| 2005/0179892 | A1 | | 8/2005 | Gerstner et al. ............. 356/318 |
| 2006/0253035 | A1 | | 11/2006 | Stern ............................ 600/476 |
| 2007/0258908 | A1 | * | 11/2007 | Lanza et al. ............... 424/9.322 |
| 2009/0297016 | A1 | | 12/2009 | Levenson et al. ............ 382/133 |

FOREIGN PATENT DOCUMENTS

| | | |
|---|---|---|
| WO | WO 98/43042 | 10/1998 |
| WO | WO 00/17808 | 3/2000 |
| WO | WO 00/31534 | 6/2000 |
| WO | WO 2005/045396 | 5/2005 |
| WO | WO2005/116597 | 12/2005 |
| WO | WO2006/031537 | 3/2006 |

OTHER PUBLICATIONS

Agard, *Optical Sectioning Microscopy: Cellular Architecture in Three Dimensions*, Annual Reviews in Biophysics and Bioengineering, vol. 13, pp. 191-219, (1984).

Joshi et al., *Maximum a Posteriori Estimate with Good's Roughness for Three-Dimensional Optical-Sectioning Microscopy*, Journal of Optical Society of America, vol. 10, No. 5, pp. 1078-1085 (1993).

Carrington et al., *Superresolution Three-Dimensional Images of Fluorescence in Cells with Minimal Light Exposure*, Science, vol. 268, pp. 1483-1487 (1995).

Wong et al., *Brushing Techniques for Exploring Volume Datasets*, pp. 429-432, Eighth IEEE Visualization 1997 (VIS'97). (1997).

Huth et al., *Fourier Transformed Spectral Bio-Imaging for Studying the Intracellular Fate of Liposomes*, Cytometry Part A, vol. 57A, pp. 10-21 (2004).

Fountaine et al., *Multispectral imaging of clinically relevant cellular targets in tonsil and lymphoid tissue using semiconductor quantum dots*, Modern Pathology, pp. 1-11 (2006).

Kriete et al., *Automated quantification of quantum-dot-labeled epidermal growth factor receptor internalization via multiscale image segmentation*, Journal of Microscopy, vol. 222(1), pp. 22-27 (2006).

Ried et al., *Simultaneous visualization of seven different DNA probes by in situ hybridization using combinatorial fluorescence and digital imaging microscopy*, proceedings of the National Academy of Sciences, vol. 89, pp. 1388-1392 (Feb. 1, 1992).

Speicher et al., *Karyotyping human chromosomes by combinatorial multi-fluor FISH*, Nature Genetics, vol. 12, pp. 368-375 (Jan. 1, 1996).

Schröeck et al, *Multicolor Spectral Karyotyping of Human Chromosome*, Science, vol. 273, pp. 494-497 (Jul. 26, 1996).

Invitation to Pay Additional Fees and Annex to Form PCT/ISA/206 Communication Relating to the Results of the Partial International Search mailed Dec. 19, 2008 in PCT/US2007/025128, filed Dec. 7, 2007.

International Search Report mailed Feb. 25, 2009 in PCT/US2007/025128, filed Dec. 7, 2007.

Written Opinion of the International Search Authority mailed Feb. 25, 2009 in PCT/US2007/025128, filed Dec. 7, 2007.

International Preliminary Report on Patentability dated Jul. 2, 2009 in PCT/US2007/025128 filed Dec. 7, 2007.

European office action dated May 26, 2010 in EP 07 874 167.5.

Robila, et al., *A parallel unmixing algorithm for hyperspectral images*, SPIE Proceedings, vol. 6384 (Oct. 2, 2006).

Rajpoot et al., *Hyperspectral Colon Tissue Cell Classification*, SPIE Medical Imaging (2004).

Battifora, H. *The multitumor (sausage) tissue block: novel method for immunohistochemical antibody testing*. Lab Invest 1986, 55:244-248.

Battifora et al., *The checkerboard tissue block, An improved multitissue control block*. Lab Invest 1998, 63:722-724.

Kononen et al., *Tissue microarrays for high-throughput molecular profiling of tumor specimens*, pp. 4:844-4:847, Nat Med 1998.

Vincent, L. et al., *Watersheds in digital spaces: An efficient Algorithm based on immersion simulations*, IEEE Transactions on Pattern Analysis and Machine Intelligence, V.13 (6) Jun. 1991 pp. 583-598.

Roerdink, J. and Meijster, A., *The Watershed Transform: Definitions, Algorithms and Parallelization Strategies*, Fundamenta Informatica, v. 41, 2001, IOS Press pp. 187-228.

Jones et al., *Methods for High-Content, High-Throughput Image-Based Cell Screening*, Proceedings of MIAAB 2006 available online at www.broad.mit.edu/~thouis/MIAABPoster.pdf.

Gang Lin et al., *A Hybrid 3D Watershed Algorithm Incorportating Gradient Cues and Object Models for Automatic Segmentation of Nuclei in Confocal Image Stacks*, Cytometry Part A, 56A:23-26 (2003).

Y. Garini et al., *Signal to Noise Analysis of Multiple Color Flourescence Imaging Microscopy*, Cytometry v. 35, pp. 214-226 (1999).

Heim and Tsien, *Engineering green fluorescent protein for improved brightness, longer wavelengths and fluorescence resonance energy transfer*. Current Biology 6:178-182(1996).

Castleman, Kenneth, *Color compensation for digitized FISH Images*. Bioimaging I 159-165 (1993).

Gothot et al., *A Strategy for Multiple Immunophenotyping by Image Cytometry: Model Studies Using Latex Microbeads Labeled with Seven Streptavidin-Bound Fluororchromes*, Cytometry 24:214-225, (1996).

Presentation of Dr. Thomas M. Grogan, XXVI Congress of the International Academy of Pathology, Hematopathology Symposium: New Technologies, Sep. 20, 2006.

U.S. Appl. No. 13/454,205, filed Apr. 24, 2012, Lett et al.

* cited by examiner

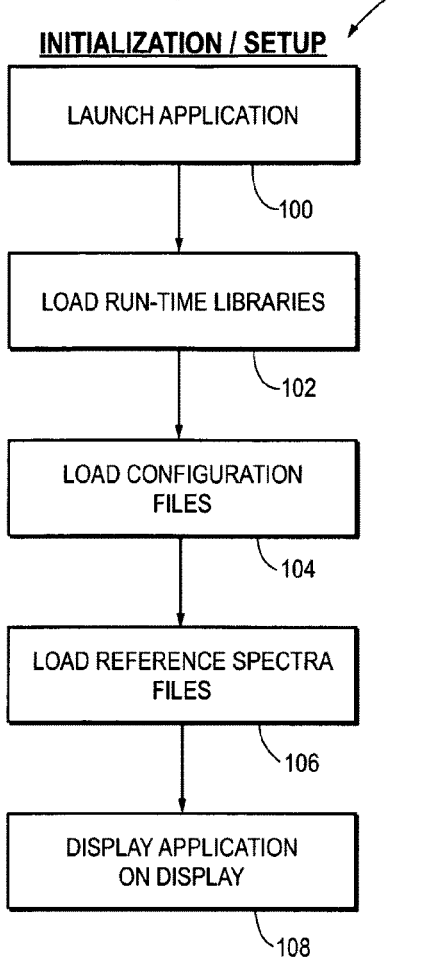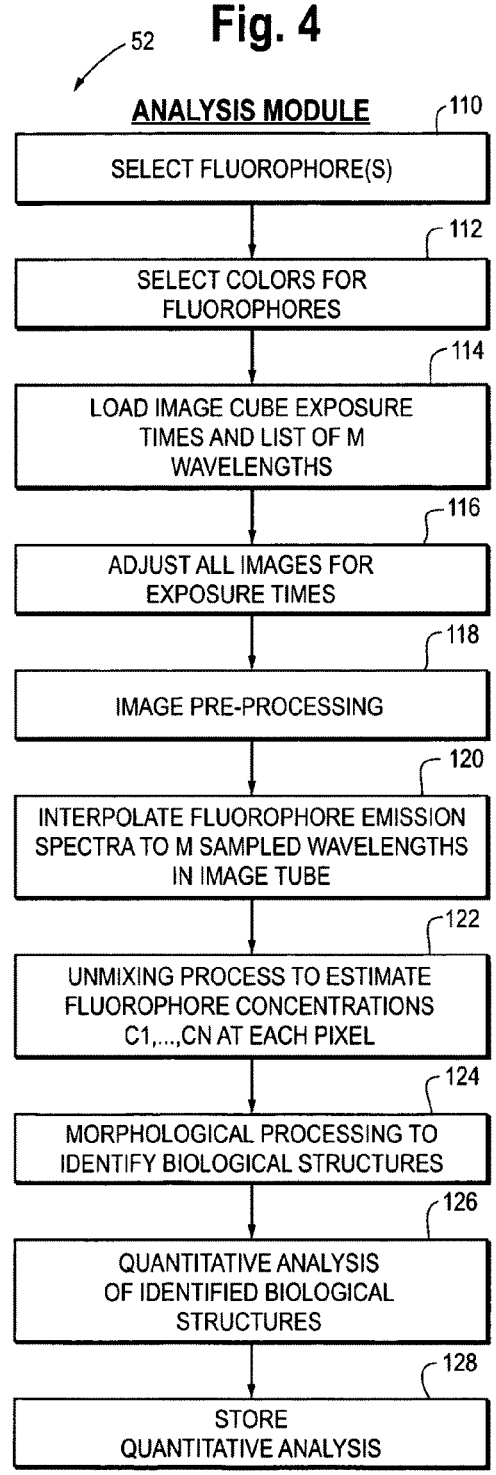

US 8,290,236 B2

QUANTITATIVE, MULTISPECTRAL IMAGE ANALYSIS OF TISSUE SPECIMENS STAINED WITH QUANTUM DOTS

PRIORITY

This application is a divisional of U.S. Ser. No. 11/999,914 filed Dec. 6, 2007, which claims priority benefits under 35 U.S.C. §119(e) to prior U.S. provisional application Ser. No. 60/876,493 filed Dec. 20, 2006, the contents of which are incorporated by reference herein.

BACKGROUND

This invention relates to the field of systems and methods for analysis of biological specimens such as tissue sections, blood, cell cultures and the like. More particularly, this invention relates to a system, method and apparatus for analysis of images of biological specimens which are stained with one or more fluorophores, at least one of which is a nano-crystalline luminescent semiconductor material known in the art as a "quantum dot." This invention also relates to methods of presentation of quantitative data resulting from such analysis to a user.

It is known in the art that biological specimens, such as tissue sections from human subjects, can be treated with a stain containing an organic fluorophore conjugated to an antibody which binds to protein, protein fragments, or other targets in the specimen. The stained specimen is then illuminated with light and the stain fluoresces. A digital camera attached to a microscope is then used to capture an image of the specimen. The areas where the fluorophore/antibody combination became bound to the target of interest (e.g., proliferation protein produced by cancerous cells) appears as colored regions in the image of the specimen, with the color of the area dictated by the fluorescence spectrum of the fluorophore applied to the specimen. In addition to the visible spectrum, the fluorescence signal may be detected in the infra-red or ultra-violet regions, depending on emission spectrum of the particular fluorophore. A stain containing two or more fluorophores can also be applied to the specimen. These methods have a variety of uses, including diagnosis of disease, assessment of response to treatment, and development of new drugs to fight disease.

More recently, quantum dots have been developed as a stain material for biological staining and imaging applications. The use of quantum dots poses several advantages over traditional organic fluorophores for use in biological staining applications. These advantages include narrow emission band peaks, broad absorption spectra, intense signals, and strong resistance to bleaching or other degradation.

Prior art references disclosing quantum dots and their application to biochemical imaging applications include U.S. Pat. Nos. 6,322,901, 5,990,749, and 6,274,323. Representative image capture and analysis systems and related methods are disclosed in the U.S. Pat. Nos. 6,215,892 and 6,403,947 and published PCT applications WO 00/31534, WO 00/17808 and WO 98/43042. Other prior art of interest includes US Patent Application Publication US 2001/0033374 A1; US Patent Application Publication 2002/0001080 A1; Fountaine et al., *Multispectral imaging of clinically relevant cellular targets in tonsil and lymphoid tissue using semiconductor quantum dots*, Modern Pathology (2006) 1-11, and Huth et al., *Fourier Transformed Spectral Bio-Imaging for Studying the Intracellular Fate of Liposomes*, Cytometry Part A, vol. 57A pp. 10-21 (2004). The entire content of the above-cited references are incorporated by reference herein.

SUMMARY

The following embodiments and aspects thereof are described and illustrated in conjunction with systems, tools and methods which are meant to be exemplary and illustrative, not limiting in scope. All questions regarding scope of the invention are to be determined with reference to the appended claims and claims hereafter introduced into the application.

In a first aspect, a system is disclosed for analysis of a biological specimen. The specimen may, for example, take the form of a tissue section obtained from a human or animal subject. The specimen may be living cellular tissue, frozen cells, tumor cells, blood, throat culture, or other; the type or nature of specimen is not particularly important. Typically, the specimen is mounted on a slide for analysis. The analysis may be for purposes of identification and study of the sample for presence of proliferation proteins or tumor cells, or for other purposes such as genomic DNA detection, messenger RNA detection, protein detection, or other. The biological specimen has between 1 and N discrete fluorophore(s) applied to the specimen, the fluorophores including at least one quantum dot. For example, the specimen may be treated with 2, 3 or 5 different quantum dots (N=2, 3 or 5 in these examples). One or more of the fluorophores applied to the specimen may be organic fluorophores.

The system includes a microscope and attached digital camera capturing images of the specimen. Each image is composed of a plurality of pixels corresponding to the individual picture elements (pixels) of the digital camera. The camera captures an image of the specimen at a plurality of discrete wavelengths. The number of wavelengths (M herein) may be 5, 10, 20 or more. The wavelengths include discrete wavelengths at which the 1 . . . N fluorophores produce a luminescent response to incident light. A data set representing two dimensional pixel data at M wavelengths is referred to herein occasionally as an "image cube."

The system further includes a workstation which includes a processing unit executing software instructions which performing certain processing steps on the images generated by the camera. These processing steps include:

a) an unmixing process, which processes the plurality of images in conjunction with reference spectral data associated with the 1 . . . N fluorophores and responsively calculates coefficients $C_1 \ldots C_N$ at each pixel location, wherein the coefficients $C_1 \ldots C_N$ are related to the concentrations of the 1 . . . N fluorophores present in the sample at each pixel location;

b) at least one morphological processing process identifying at least one biological structure in the specimen;

c) a quantitative analysis process calculating fluorophore concentrations for the biological structures identified by process b) from the coefficients $C_1 \ldots C_N$; and d) a display process for displaying the results of the quantitative analysis process c) on a display associated with the workstation.

A variety of display tools are disclosed by which a user may interact with the system and obtain displays of quantitative results from the specimen. In one embodiment, the biological structures which are identified by the morphological processing process are cells or cellular components. The morphological processing process measures the size of the biological structures, and counts the number of biological structures identified in the specimen. The results of the quantitative analysis process are presented as a histogram of the number of biological structures sorted by size of the biological structures. The histograms may also include histograms of the size distribution of cells having a positive signal for each of the 1 . . . N fluorophores applied to the specimen.

In another embodiment, the display process includes a feature allowing a user to select a segment of an image of the specimen displayed on the display (e.g., a region of the sample having a high concentration of cells with a high fluorescent signal) and the display process displays quantitative results for the selected segment of the image. As a further enhancement, the quantitative results are displayed as a plot of concentration of one quantum dot as a function of concentration of a second quantum dot for cells positive for both quantum dots. Such a plot can visually be represented as a scatter plot. Scatter plots can be displayed for either the entire image or any selected sub-segment of the slide.

In another embodiment, the coefficients $C_1 \ldots C_N$ are scaled to absolute concentrations of the fluorophores in the specimen (e.g., nanomols per liter, number of quantum dots per cell, or other system of units). Furthermore, the plots of concentration of fluorophores can be expressed in units of absolute concentrations.

The display of the quantitative results may include display of an image of the specimen on the same display. The image can be constructed from one or more of the M images, or, more preferably, from one or more of the coefficients $C_1 \ldots C_N$. It will be recalled that the coefficients are obtained by the unmixing processes and are known for each pixel. For example, if the user is studying a histogram of the size distribution of cells have positive signal for a quantum dot fluorophore whose emission spectrum peaks at 625 nm, the display may simultaneously show an image of the specimen with the image generated from the coefficient $C_i$ which corresponds to the 625 nm quantum dot fluorophore. In other words, the image masks (omits) the signal contribution from all other fluorophores which may be present in the sample and only reveals the signal from the 625 nm fluorophore. The quantitative results may further include statistical data for the segment of the image selected by the user.

In one embodiment the display process further provides a tool by which color intensity for one or more selected fluorophores can be selectively weighted by the user to thereby change the appearance of the image on the display. For example, the user may wish to view an image of the specimen that reveals the distribution of 605 nm and 625 nm quantum dots in the specimen. When such image is displayed, a tool is presented by which a user can selectively weight (or attenuate), either the 605 nm quantum dot signal or the 625 nm quantum dot signal. The weighting may be used for example to strengthen a weak fluorophore signal and allow the user to more readily perceive the distribution of the fluorophore in the biological structures (e.g., cells) in the specimen.

The display process may combine the various analytical features and provide a variety of different tools for analyzing the specimen. For example, the display process may include processes for displaying i) an image of the specimen constructed from one or more of the coefficients $C_1 \ldots C_N$ (either an image of the entire specimen or some sub-segment of the specimen); ii) a histogram of biological structures identified in the image in i) sorted by size of the biological structures, for at least at least one of the fluorophores applied to the sample; and iii) one or more scatter plots of concentration of one of the fluorophores as a function of concentration of one of the other fluorophores, for biological structures having a positive signal for both fluorophores. These features may be combined with the display of additional statistical data, tools for selection of portions of an image conducting further quantitative analysis, and still other features.

In still another embodiment, the display process includes a feature by which a user may select a portion of a scatter plot, histogram, or other visualization of the quantitative data and conduct further quantitative analysis on the portions of the specimen corresponding to the selected portion of the scatter plot, histogram or other visualization. For example, a user may select the portion of a histogram corresponding to larger cells with relatively high concentrations of a particular fluorophore (e.g. 625 nm quantum dot). The display process creates a new display which displays additional quantitative data for the larger cells in the histogram which were selected by the user. Such quantitative data may take a variety of forms, such has a new scatter plot showing the concentration of the 605 nm quantum dot as a function of the concentration of the 625 nm quantum dot, for the cells which correspond to the portion of the histogram selected by the user.

Additionally, the display process may display an image of the specimen with the biological structures associated with the selected portion of the histogram, scatter plot or other visualization, with the biological structures highlighted, e.g. in a contrasting color. The image can be constructed from the concentration coefficient corresponding to the 625 nm quantum dot, the 605 quantum dot, other fluorophore present in the sample, e.g., autofluorescence, combination thereof, or other.

In yet another aspect of this disclosure, a method is provided for analysis of a biological specimen in which between 1 . . . N quantum dots are applied to the specimen. The method includes the steps of:

(a) capturing a set of images of the specimen with a camera coupled to a microscope at M different wavelengths, where M is an integer greater than 2, the images arranged as an array of pixels;

(b) determining, from the set of M images, coefficients $C_1 \ldots C_N$ for each pixel, wherein the coefficients $C_1 \ldots C_N$ are related to the concentrations of the 1 . . . N quantum dots present in the specimen imaged by each pixel;

(c) morphologically processing an image constructed from one or more of the coefficients $C_1 \ldots C_N$ to identify cells or cellular components in the specimen, (d) conducting a quantitative analysis of cells or cellular components identified in step (c) from the coefficients $C_1 \ldots C_N$; and (e) displaying the results of the quantitative analysis process (d) on a display of a workstation.

The quantitative analysis and displaying steps may incorporate one or more of the quantitative analysis and display features highlighted above in the discussion of the system aspect of this invention.

In still another aspect of this disclosure, the invention can be characterized as biological specimen analysis apparatus taking the form of a machine readable storage medium (e.g., hard disk, CD, or other medium) which contains a set of software instructions for execution by a processing unit, e.g., a computer workstation. The processing unit has access to an image cube of a specimen stained with one or more quantum dots and imaged with a camera coupled to a microscope. The image cube may be a set of M images of the sample taken at M different wavelengths, where M is an integer greater than 2. The images are arranged as an array of pixels. The set of images can be stored locally on the processing unit, obtained over a network, or also stored on the machine-readable storage medium. The instructions comprise a set of instructions for:

(a) determining from the set of M images coefficients $C_1 \ldots C_N$ for each pixel, wherein the coefficients $C_1 \ldots C_N$ are related to the concentrations of the one or more quantum dots present in the specimen imaged by each pixel;

(b) morphologically processing an image of the specimen to identify cells or cellular components in the specimen, (c) conducting a quantitative analysis of the specimen including calculating quantum dot concentrations for the cells or cellular components identified in step (b) from the coefficients $C_1 \ldots C_N$; and (d) generating data for display of the results of the quantitative analysis process (c) on a display associated with the processing unit.

As with the method aspect of the invention, the software instructions may incorporate one or more of the quantitative analysis and display features highlighted above in the discussion of the system aspect of this invention.

The image analysis, quantitative analysis and display methods are preferably designed to be used with a variety of commercially available imaging platforms, staining systems and workstations. Accordingly, in one possible embodiment the software instructions can be provided as a separate product that enables existing imaging equipment and computer workstations to practice the invention, without necessitating purchase of expensive new hardware. Thus, the software instructions stored on a machine readable medium (e.g., CD) have their own special utility and advantage.

In addition to the exemplary aspects and embodiments described above, further aspects and embodiments will become apparent by reference to the drawings and by study of the following detailed descriptions.

BRIEF DESCRIPTION OF THE DRAWINGS

FIG. 3 is a flow chart showing a sequence of processing steps performed by the initialization and set-up module of FIG. 2.

FIG. 4 is a flow chart showing a sequence of processing steps performed by the analysis module of FIG. 2.

FIG. 17 also shows the spectra for the region of the specimen represented in the three images.

DETAILED DESCRIPTION

System and Software Overview

Figure 1:
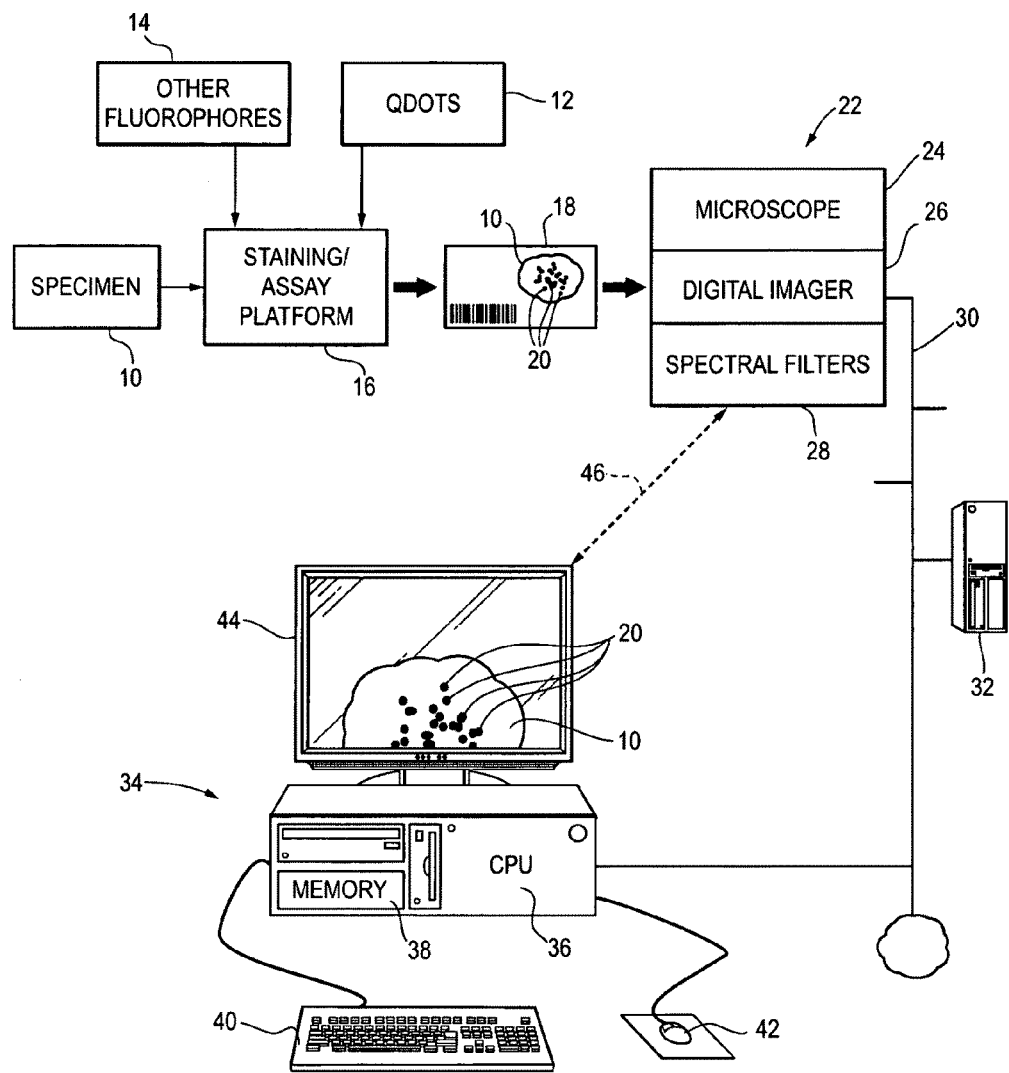
FIG. 1 is block diagram of a system for analyzing a biological specimen. The system includes a digital camera, a microscope, and a workstation having a display and a memory storing software instructions for processing images of the specimen captured by the camera.

FIG. 1 is a block diagram of a system for analysis of a biological specimen 10. The specimen 10 may, for example, take the form of a tissue section obtained from a human or animal subject, such as a formalin-fixed, paraffin-embedded tissue sample. The specimen may be living cellular tissue, frozen cells, tumor cells, blood, throat culture, or other; the type or nature of specimen is not particularly important.

Typically, the specimen is mounted on a slide 18 or other device for purposes of imaging by a camera system platform 22. Computer analysis of images of the specimen is performed in a workstation 34 in accordance with the present disclosure. The analysis may be for purposes of identification and study of the sample for presence of proteins, protein fragments or other markers indicative of cancer or other disease, or for other purposes such as genomic DNA detection, messenger RNA detection, protein detection, detection of viruses, detection of genes, or other.

The biological specimen 10 is stained by means of application of a stain containing one or more different fluorophore(s). The number N of fluorophores that are applied to the specimen can vary, but will typically be between 2 and say 10. The fluorophores may comprise one or more nano-crystalline semiconductor fluorophores (i.e., quantum dots) 12, each producing a peak luminescent response in a different range of wavelengths. Quantum dots are described in the patent and technical literature, see for example U.S. Pat. Nos. 6,322,901, 5,990,749, and 6,274,323. The term "quantum dot" is intended to be broadly read to encompass such structures generally. Quantum dots, including conjugated quantum dots, are commercially available from Invitrogen Corp., Evident Technologies, and others.

For example, the specimen 10 may be treated with 2, 3 or 5 different quantum dots (N=2, 3 or 5 in this example), for example quantum dots which produce a peak luminescent response at 525, 600 and 625 nm. One or more of the fluorophores applied to the specimen may be organic fluorophores 14 (e.g., DAPI, Texas Red), which are well known in the art. Thus, the system of FIG. 1 can be used with a specimen which is stained with just quantum dots, with quantum dots in combination with conventional organic fluorophores, or just conventional organic fluorophores. It is noted that quantum dots have several important advantages over conventional organic fluorophores. In practice, the quantum dots or other fluorophores are conjugated to an antibody, which is designed to bind to a target in the specimen, such as a protein.

In typical practice, the specimen is processed in an automated staining/assay platform 16 which applies a stain containing quantum dots and/or organic fluorophores to the specimen. There are a variety of commercial products on the market suitable for use as the staining/assay platform, one example being the Discovery™ product of the assignee Ventana Medical Systems, Inc.

After preliminary tissue processing and staining in the platform 16, the slide 18 containing the specimen 10 is supplied to a camera system platform 22. The platform 22 includes a light source for illuminating the specimen 10 at wavelengths intended to produce a luminescent response from the fluorophores applied to the specimen. In the case of quantum dots, the light source may be a broad spectrum light source. Alternatively, the light source may comprise a narrow band light source such as a laser. The camera platform also includes a microscope 24 having one or more objective lenses and a digital imager (camera) 26 which is coupled to the microscope in order to record high resolution, magnified digital images of the specimen. As will be explained below, the specimen 10 is imaged by the camera 26 at a plurality of different wavelengths. In order to capture images at a plurality of different wavelengths, the camera platform 22 includes a set of spectral filters 28. Other techniques for capturing images at different wavelengths may be used. The camera 26 may take the form of a charge-coupled device imager sensitive to light in a band covering the luminescent response spectra of the fluorophores, e.g., between 400 and 900 nm. Camera platforms suitable for imaging stained biological specimens are known in the art and commercially available from companies such as Zeiss, Canon, Applied Spectral Imaging, and others, and such platforms are readily adaptable for use in the system, methods and apparatus of this invention.

The camera 26 images the specimen at a plurality (M) of discrete wavelengths and responsively generates an image of the specimen at each of the M wavelengths. Each of the images is composed of a plurality of pixels corresponding to the individual picture elements (pixels) in the digital imager 26. The wavelengths at which the specimen is imaged includes wavelengths at which the 1 . . . N fluorophores present in the sample produce a luminescent response to incident light. For example, suppose the specimen is stained with two quantum dots, having a peak luminescent response at 625 nm and 605 nm. Suppose further that the nominal (reference) spectra of such quantum dots has a Gaussian distribution with appreciable response between 575 and 750 nm (see for example the reference quantum dot spectra in FIG. 6 and the discussion below). Therefore, the camera 26 is operated to image the specimen at say 10, 15, or 20 different wavelengths between 575 and 750 nm. As an example, the camera (and any attendant spectral filters 28) is operated so as to capture images of the specimen at 575, 600, 625, 650, 675, 700, 725 and 750 nm, such wavelengths overlapping the reference spectra of the 605 and 625 nm quantum dot fluorophores at wavelengths where the fluorophores produce a significant luminescent response. M=8 in this example.

The data resulting from a set of M images of the specimen (one taken at each of the M wavelengths) is referred to herein as an "image cube". Referring again to FIG. 1, the image cube is supplied to the workstation 34, either via a cable connection between the camera imaging platform 22 and the workstation 34 (indicated at 46) or via a computer network 30 connecting the camera imaging platform 22 to the workstation 34 or using any other medium that is commonly used to transfer digital information between computers. The image cube can also be supplied over the network 30 to a network server 32 or database for storage and later retrieval by the workstation 34.

The workstation 34 includes a central processing unit 36 and a memory 36, user input devices in the form of a keyboard 40 and mouse 42, and a display 44. As will be explained in the following discussion, the processor 36 executes program instructions loaded in to the memory 38 which perform analysis of the image cube, morphological processing of the images or image data derived from such images, quantitative analysis, and display of quantitative results to a user operating the workstation 34.

Figure 2:
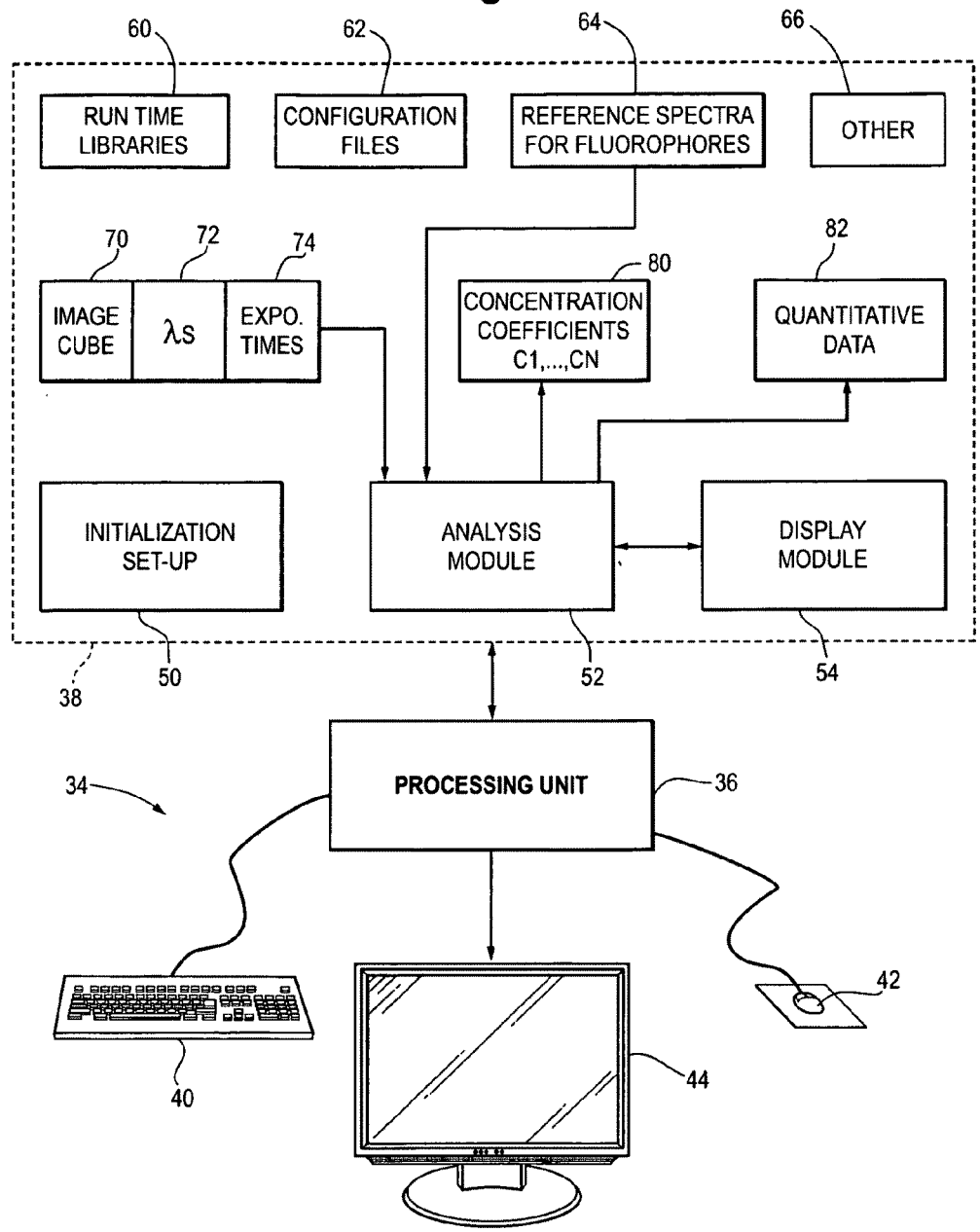
FIG. 2 is a more detailed block diagram of the workstation of FIG. 1, showing software modules which are stored in memory of the workstation.
Figure 6:
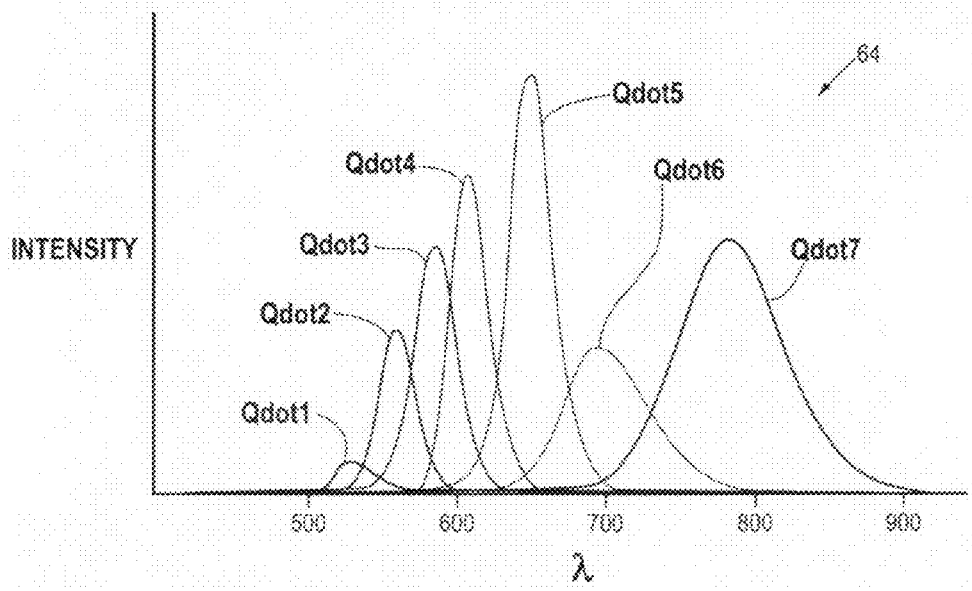
FIG. 6 is a graph of the reference emission spectra of seven quantum dot fluorophores, one or more of which are applied to the specimen. The spectra of FIG. 6 are stored in the workstation and applied to the image cube of FIG. 5 in a spectral unmixing algorithm in order to calculate coefficients $C_1 \ldots C_N$ at each pixel location. The coefficients $C_1 \ldots C_N$ are related to the concentrations of the 1 ... N fluorophores (quantum dots) present in the sample at each pixel location.

FIG. 2 is a more detailed illustration of the workstation of FIG. 1 showing in greater detail certain software modules and data stored in the memory 38. The memory includes three main software instruction modules, namely an initialization and set-up module 50 (steps of which are shown in FIG. 3), an analysis module 52 (steps of which are shown in FIG. 4) and a display module 54, the operation of which will be described in conjunction with FIGS. 7-18. The memory 38 further stores certain other data which is used or operated on by the modules 50, 52 and 54, namely run-time libraries 60, configuration files 62, and reference spectral data 64 for the 1 . . . N fluorophores which are applied to the sample. An example of the reference spectra 64 for an assay using seven different quantum dots (Qdot 1 . . . Qdot 7) is shown in FIG. 6. The reference spectra 64 are used in the spectral unmixing algorithm in the analysis module 52, as will be explained in greater detail below. The spectra 64 of FIG. 6 are offered by way of example only to show that different quantum dots have different spectra, including a different wavelength of peak luminescent response and different peak intensity under the same illumination conditions. The spectral data 64 will thus vary depending on the particular quantum dots that are used in an assay. The spectral data of FIG. 6 can be obtained from the manufacturer of the quantum dots or alternatively obtained by testing examples of the quantum dots using appropriate equipment.

The memory 38 further stores the image cube 70 comprising the M images of the spectrum, taken at M different wavelengths. The memory further stores a list 72 of the wavelengths at which the specimen was imaged, and a list 74 of the exposure times at each of the wavelengths. The image cube and lists 72 and 74 are inputs to the analysis module 52.

The memory further stores the calculated concentration coefficients $C_1 \ldots C_N$ (item 80). The coefficients are outputs from the analysis module 52 and are used by quantitative analysis routines in the module 52. The module 52 further produces as additional output quantitative data 82 which is stored in memory. The concentration coefficients 80 and quantitative data 82 are used by the display module 54 to display the quantitative data to the user in a convenient and user-friendly fashion as will be explained below.

One aspect of the processing performed by the analysis module 52 in the workstation 34 is a spectral unmixing process by which the plurality of images in the image cube 70 are processed with reference spectral data 64 associated with the 1 . . . N fluorophores (FIG. 6) in order to produce an estimate of coefficients $C_1 \ldots C_N$ at each pixel location. The coefficients $C_1 \ldots C_N$ are related to the concentrations of the 1 . . . N fluorophores present in the sample at each pixel location. The coefficients $C_1 \ldots C_N$ can be scaled to absolute fluorophore concentrations. The coefficients also can be scaled in arbitrary units and used to represent concentration in terms of illumination intensity, either relative or absolute.

The term "pixel location" in the context of the coefficients $C_1 \ldots C_N$ will be understood to refer to the individual locations in each of the images which also corresponds to the individual pixels of the digital camera 26. For example, if the digital camera 26 is constructed as an array of pixels arranged in 1 . . . i rows and 1 . . . j columns of pixels, each pixel of the camera imaged the specimen M times.

For each pixel, the spectral unmixing process calculates coefficients $C_1 \ldots C_N$ which relate to the concentration of each fluorophore to all of the M images for that pixel. When applied to the entire image cube, the spectral unmixing process determines, in an overall sense, the relative contributions of each of the 1 . . . N fluorophores present in the sample to the resulting images, and in particular their concentrations, either in relative terms or with appropriate scaling in absolute terms. The spectral unmixing process performs such calculations for each of the pixels. A variety of unmixing processes can be used, and a linear spectral unmixing process as described in Huth et al., *Fourier Transformed Spectral Bio-Imaging for Studying the Intracellular Fate of Liposomes*, Cytometry Part A, vol. 57A pp. 10-21 (2004) is considered preferred. This process will be discussed in greater detail below.

The workstation further includes software instructions as part of the analysis module 52 which performs at least one morphological process in order to identifying one or more biological structures in the specimen. Such structures can be whole cells (indicated at 20 in FIG. 1), or cellular components such as cell membranes, nuclei, cytosol, mitochondria, genes, DNA fragments, RNA, messenger RNA entities, or other, and are identified by shape or other characteristics which can be determined by using known morphological or similar image processing techniques. The morphological processing to identify such structures can be performed on any one of the images, all of the images, or more preferably an image constructed from one or more of the identified coefficients $C_1 \ldots C_N$ In still another possible variation, the specimen is stained with Hematoxylin and Eosin (H and E) and the morphological process identifies the biological structures of interest from an image of the sample stained with H and E.

A variety of morphological processing techniques are known to persons skilled in the art which can be used to identify the biological structures in an image of the sample. Examples include a multi-scale approach, such as described in Kriete, A et al., *Automated quantification of quantum-dot-labeled epidermal growth factor receptor internalization via multiscale image segmentation*, Journal of Microscopy, v. 222(1) 22-27 (April 2006); an active contour (snake) approach, described in Kass, A. Witkin, and D. Terzopoulos. *Snakes: Active contour models*. International, Journal of Computer Vision, 1:321-332, 1988; a level set approach, described in J. A. Sethian, *Level Set Methods: Evolving Interfaces in Geometry, Fluid Mechanics, Computer Vision and Materials Sciences*. Cambridge Univ. Press, 1996; a contour closure approach described in Mahamud, S et al., *Segmentation of Multiple Salient Closed Contours from Real Images*, IEEE Transactions On Pattern Analysis And Machine Intelligence, Vol. 25, No. 4, April 2003, and a Watershed approach (currently used in the illustrated embodiment), described in Vincent, L. et al., *Watersheds in digital spaces: An efficient algorithm based on immersion simulations*, IEEE Transactions on Pattern Analysis and Machine Intelligence v. 13(6) June 1991 pp. 583-598, see also the review article on Watershed: Roerdink, J. and Meijster A., *The Watershed Transform: Definitions, Algorithms and Parallelization Strategies*", Fundamenta Informatica v. 41, 2001, IOS Press pp. 187-228. Other techniques can be used, including those disclosed in the following papers: Thouis R. Jones et al., *Voroni-Based Segmentation of Cells on Image Manifolds*, in CVBIA, ser. Lecture Notes in Computer Science, Y. Liu et al. Eds., vol. 3765 Springer-Verlag, 2005 pp. 535-543; the poster paper of Thouis R. Jones et al., *Methods for High-Content, High-Throughput Image-Based Cell Screening*, Proceedings of MIAAB 2006 available on-line at www.broad.mit.edu/~thouis/MIAABPoster.pdf; and Gang Lin et al., *A Hybrid 3D Watershed Algorithm Incorporating Gradient Cues and Object Models for Automatic Segmentation aof Nuclei in Confocal Image Stacks*, Cytometry Part A, 56A:23-26 (2003).

Once the biological structures are identified in the specimen using these processes, a routine in the analysis module 52 counts the structures in the entire specimen, counts the structures positive for each of the fluorophores applied to the specimen, measures their size, and stores the location in the image of each of such structures. The storage of such quantititative data is represented in FIG. 2 at 82.

Part of the analysis module 52 includes a quantitative analysis process which, among other things, calculates the fluorophore concentrations for the biological structures 20 (FIG. 1) for each of the fluorophores, using the coefficients $C_1 \ldots C_n$ which were obtained in the spectral unmixing process. For example, for each of the identified biological structures 20 (e.g., cells), the quantitative analysis sums the total fluorophore concentrations for each of the N fluorophores for those pixels representing the biological structures. Consider, for example, a specimen containing cancer cells stained with six quantum dots conjugated to antibodies which are designed to attach to six different proliferation proteins which may be found in the specimen. Consider further that two of the quantum dots (605 nm and 625 nm) were bound to the cells in the specimen but the remaining four quantum dots were not bound to any cells in the specimen. The morphological processing processes identify all cells in the specimen which produced a non-zero luminescent response for the 605 and 625 quantum dots. (A threshold other than zero could of course be specified, such as 10 or 30 on a scale of 0-255 with 8-bit quantization of the signal level from the camera 26.) The pixels coordinates for such cells are identified. The values of coefficients $C_i$, $C_j$ associated with the 605 and 625 quantum dots are recorded for such pixel coordinates, and optionally scaled to intensities, absolute concentrations, or other value. The resulting quantitative data, along with pixel addresses for the cells, is stored in memory in the workstation.

The quantitative analysis module may also calculate other statistics for the sample, including (a) counts of the number of cells; (b) counts of the number of cells with positive signal for each of the fluorophores; c) sorting the cells into histograms organized by size, presence of one or more fluorophores or other characteristic; (d) calculating mean, median and standard deviation of cell sizes; (d) measurements of fluorophore concentration (intensity) for the identified biological structures, and still others. Such additional quantitative data is also represented in FIG. 2 at 82.

Figure 11:
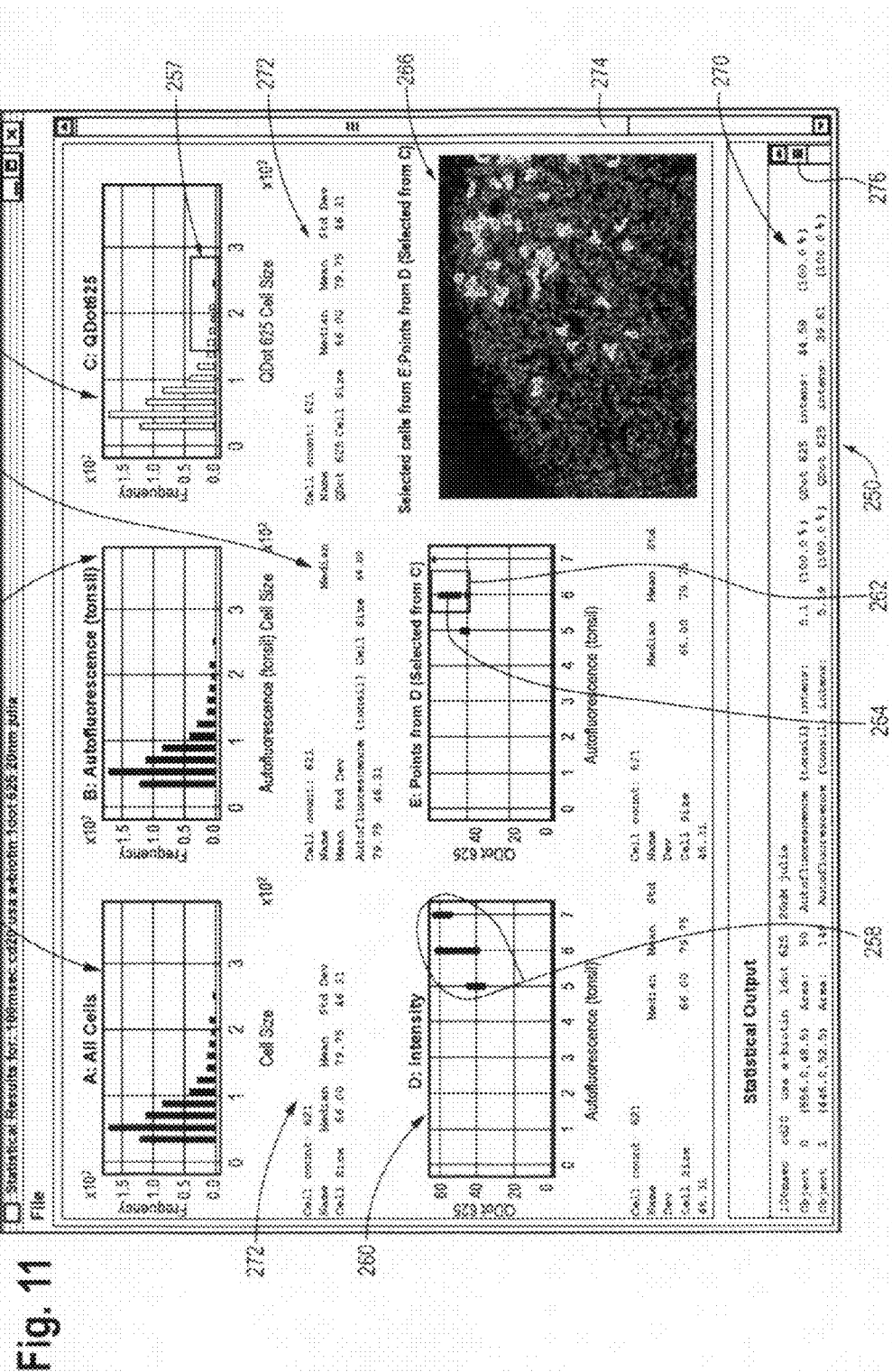
FIG. 11 is an illustration of a display on the workstation showing a set of quantitative data which is presented to the user for the specimen, including histograms, scatter plots, statistical data and image data.

The workstation further includes a display process or module 54 for displaying the results of the quantitative analysis process c) on a display 44 associated with the workstation. A variety of methods and tools for display of quantitative data from the specimen are contemplated and will be described with reference to FIG. 11-18 in the following discussion. As one example, as shown in FIG. 11, the results of the quantitative analysis process are presented as a histogram of the number of biological structures sorted by size of the biological structures, for each of the 1 . . . N fluorophores applied to the specimen.

Figure 14:
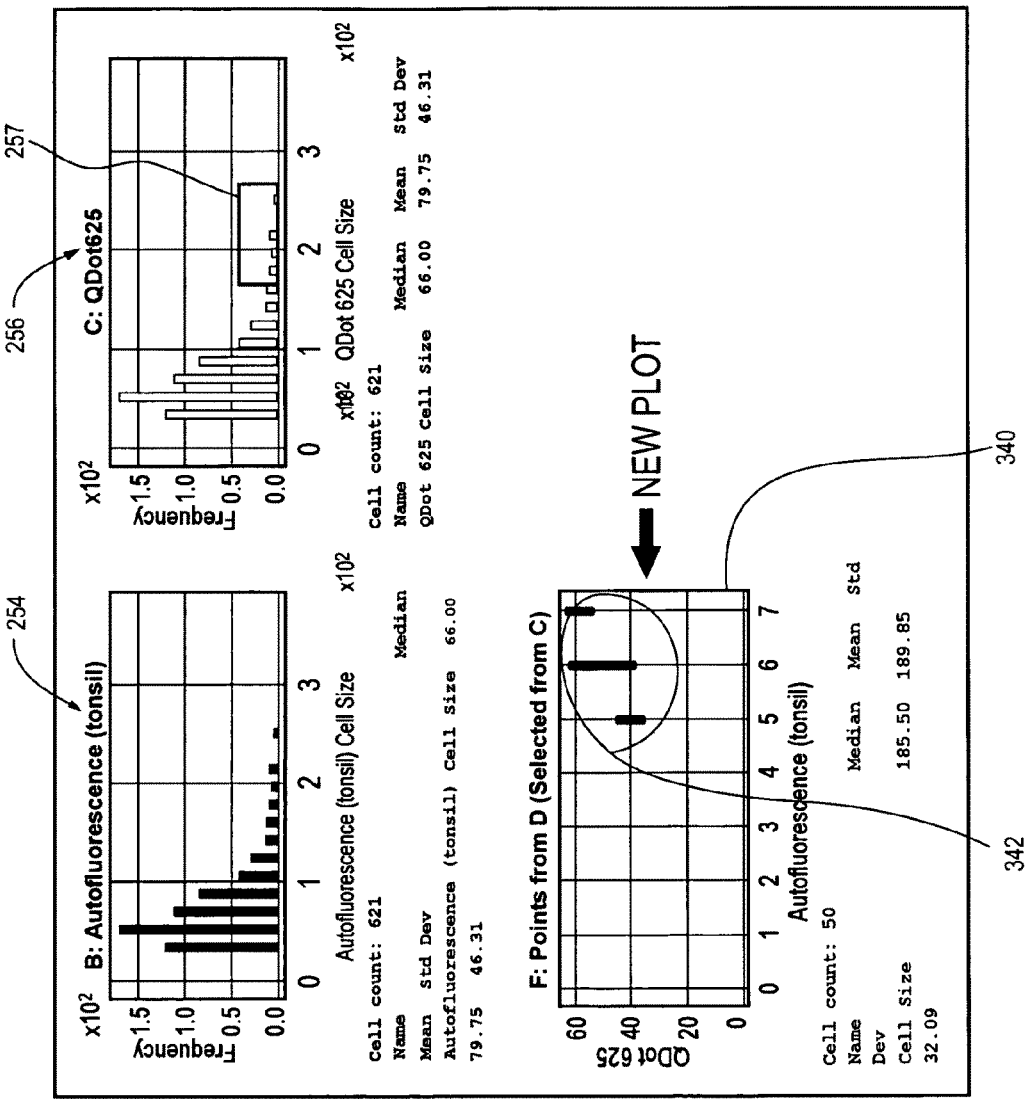
FIG. 14 is an illustration of a display of the workstation showing a scatter plot providing additional quantitative analysis of the selected sub-population of cells selected by the user in FIG. 13.

In another embodiment described later in conjunction with FIGS. 15 and 16, the display process includes a feature allowing a user to select a segment of an image of the specimen displayed on the display (e.g., a region of cells having a particularly high fluorescent signal) and the display process displays quantitative results for the selected segment of the image. As another example, as shown in FIGS. 11 and 14, the quantitative results that are displayed can take the form of a plot of concentration of one fluorophore (e.g. 605 quantum dot) as a function of concentration of a second fluorophore (e.g., 625 quantum dot) for those cells positive for both fluorophores, either in a selected segment of the image, or in an overall image. Such a plot can visually be represented as a scatter plot, for example as shown in FIG. 18.

In another embodiment, the coefficients $C_1 \ldots C_N$ are scaled to absolute concentrations of the fluorophores in the specimen (e.g., nanomols per cubic micron, number of quantum dots per cell, or other system of units). Furthermore, the plots of concentration of fluorophores, or the histograms, or other reports or formats of quantitative data for the specimen, can be expressed in terms of absolute concentrations of fluorophores present in the specimen, or selected portions of the specimen.

Figure 18:
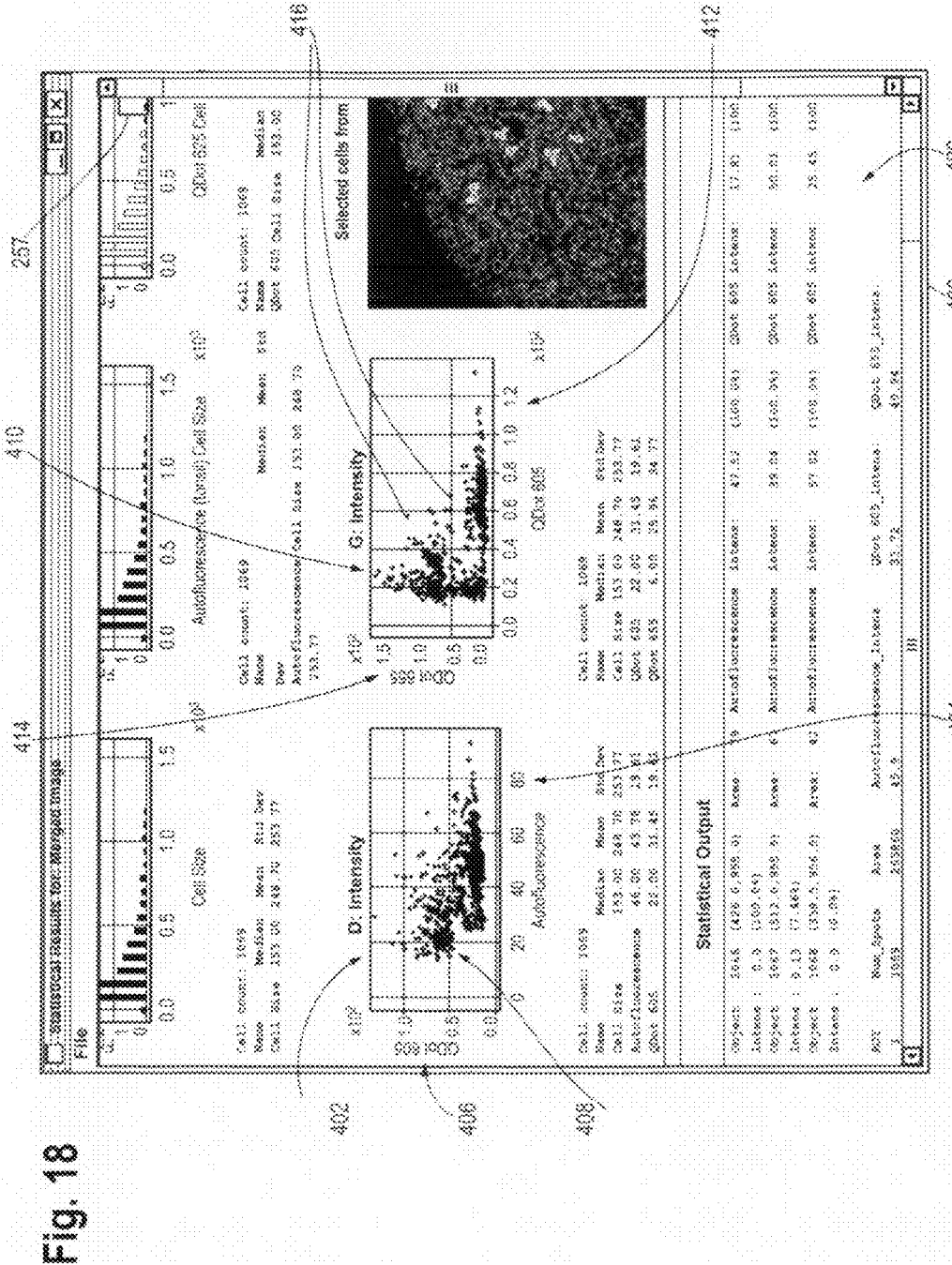
FIG. 18 is another illustration of a display presented on the workstation showing quantitative data from the specimen in the form of histograms, scatter plots, statistical data, and image data.

As shown for example in FIGS. 11 and 18, the display of the quantitative results may include display of an image of the specimen on the same display. The image can be constructed from one or more of the M images. More preferably, the image that is displayed simultaneous with the quantitative data is constructed from one or more of the coefficients $C_1 \ldots C_N$, it being recalled that such coefficients are obtained in the unmixing processes and are determined for each pixel. For example, if the user is studying a histogram of the size distribution of cells have positive signal for a 625 nm quantum dot fluorophore, the display may simultaneously show an image of the specimen with the image generated from the coefficient $C_i$ which corresponds to the 625 nm quantum dot fluorophore. Such image may be of the entire specimen, or a selected portion of the specimen. In other words, the image masks (omits) the luminescent response from all the other fluorophores which may be present in the specimen, and only reveals the contribution of the 625 nm fluorophore. The quantitative results may further include statistical data for the segment of the image selected by the user.

In a still further example, the display process provides a tool by which color intensity for one or more selected fluorophores can be selectively weighted by the user to thereby change the appearance of the image on the display. For example, the user may wish to view an image of the specimen that reveals the distribution of cells positive for the 605 nm and 625 nm quantum dots in the specimen. When such image is displayed, a tool is presented by which a user can selectively weight (or attenuate), either the 605 nm quantum dot signal or the 625 nm quantum dot signal. The weighting may be used for example to strengthen a weak fluorophore signal and allow the user to more readily perceive the distribution of the fluorophore in the biological structures (e.g., cells) in the specimen.

The display process may combine the various analytical features and provide a variety of different tools for analyzing the specimen. For example, the display process may includes processes for displaying i) an image of the specimen constructed from one or more of the coefficients $C_1 \ldots C_N$ for each pixel; ii) a histogram of biological structures identified in the image in i) sorted by size of the biological structures, for at least at least one of the fluorophores applied to the sample; and iii) one or more scatter plots of concentration of one of the fluorophores as a function of concentration of one of the other fluorophores, for cells or other biological structures positive for both fluorophores. An example of such as display is shown in FIGS. 11 and 18. These features may be combined with the display of additional statistical data, tools for selection of portions of an image conducting further quantitative analysis, and still other features.

In still another embodiment, the display process further includes a feature by which a user may select a portion of a scatter plot or a histogram, e.g., by drawing a box around the portion of the histogram or scatter plot using a mouse, and conduct further quantitative analysis on the portions of the specimen (e.g., particular cells) corresponding to the selected portion of the scatter plot or histogram. For example, a user may select the portion of a histogram corresponding to larger cells with relatively high concentrations of a particular fluorophore (e.g: 625 nm quantum dot). The display process creates a new display which displays additional quantitative data for the larger cells in the histogram which were selected by the user. Such quantitative data may take a variety of forms, such has a new scatter plot showing the concentration of the 605 nm quantum dot as a function of the concentration of the 625 nm quantum dot, for the cells which correspond to the portion of the histogram selected by the user. Additionally, the display process may display an image of the specimen with the biological structures associated with just the cells in the selected portion of the histogram presented in the image and highlighted, e.g., in a contrasting color. Such image could be constructed from the concentration coefficient $C_i$ corresponding to the 625 nm quantum dot, the 605 quantum dot, other fluorophore present in the sample, autofluorescence, combination thereof, or other.

The above-described software processes will now be described in greater detail with reference to FIGS. 3-18. As an initial step, the specimen is processed and stained with one ore more fluorophores (e.g., up to N quantum dots, where N may for example be 2, 5, 10 or more), and then imaged at the M wavelengths as described above. The resulting image cube, list of wavelengths and exposure times at each wavelength are stored in the memory 38 of the workstation 34.

Figure 5:
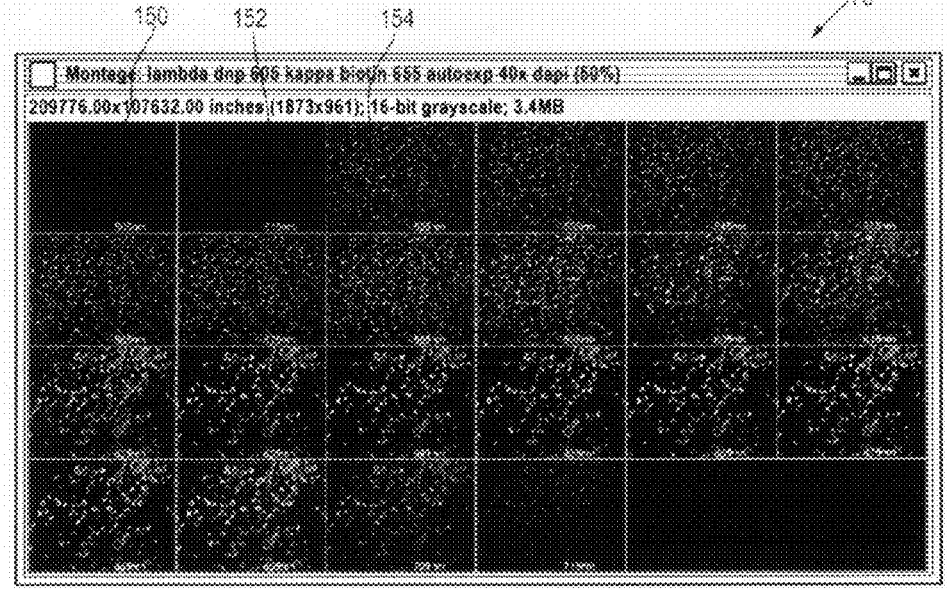
FIG. 5 is an illustration of a set of images (M=22) of a slide containing a biological specimen, each of the images captured by the camera of FIG. 1 at a discrete wavelength; data from the set of images of FIG. 5 are referred to herein occasionally as an "image cube."

FIG. 5 is an illustration of an example of one image cube 70, consisting of twenty-two discrete images 150, 152, 154 ... of the specimen at different wavelengths (M=22). The data representing the image cube 70 is obtained by the camera 26 of FIG. 1. The wavelengths $\lambda_1 \ldots \lambda_M$ are selected so that they overlap the portions of the reference spectra for the fluorophore(s) applied to the sample where there is a significant luminescent response from the fluorophore(s). For example, image 150 is an image at 505 nm, image 152 is an image of the specimen at 515 nm, image 154 is an image of the specimen at 525 nm, and the remaining 19 images obtained at 10 nm increments up to 715 nm. The 22 wavelengths overlap substantially the reference spectra for Qdot 1 ... Qdot 5 of the reference spectra of FIG. 6.

The camera 26 (FIG. 1) can use any convenient filtering technique to acquire the spectral images forming the image cube, including the use of physical filters 28, e.g., Liquid Crystal Display (LCD) spectral filters, or other types of filters.

Each image is captured for an appropriate exposure interval, depending on the sensitivity of the camera and the intensity of the illumination source. Such. exposure interval may for example be from between 100 milliseconds and 5 seconds per sampled wavelength. The exposure interval at each wavelength is stored and supplied to the workstation.

A. Initialization and Set-Up Module 50 (FIG. 3)

The initialization and set up module 50, analysis module 52 and display processes 54 of FIG. 2 are part of an application which is launched when the user clicks on an icon associated with the application on the desktop of the workstation display. The initialization and set-up module 50 is invoked when the application is launched, indicated at 100 in FIG. 3. The initialization and set-up module performs initial tasks that do not require user involvement. The details of the module are not particularly pertinent to the present invention and therefore many details are omitted for the sake of brevity. Basically, with reference to FIG. 3, the module 50 includes a step 102 which loads run-time libraries 60 (FIG. 2) which are stored in memory, and which may include image processing subroutines and other code modules ancillary to the operation of the system. At step 104, the module 104 loads configuration files, which may contain data pertinent to the particular imaging system being used, data pertinent to the specimen being analyzed, and other configuration files. At step 106, the library of reference spectra data (FIG. 2, 64) for the known fluorophores is loaded. At step 108, a initial screen is presented on the display 44 to the user that allows the user to interact with the application, and take initial steps to view the quantititative data, such as select a specimen image set for processing, e.g., using a drop-down menu or other tool, select colors for individual fluorophores, identify fluorophores which were applied to the sample, view images of the specimen, view quantitative data, etc.

B Analysis Module 52 (FIG. 4)

The analysis module 52 of FIG. 2 will be described in greater detail in conjunction with the flow chart of FIG. 4 and FIGS. 5, 6 and 8. FIG. 4 shows a sequence of individual sub-routines or steps (processing instructions) which are performed in the module 52 in order to extract quantitative data from the images of the specimen for display on the workstation.

Figure 8:
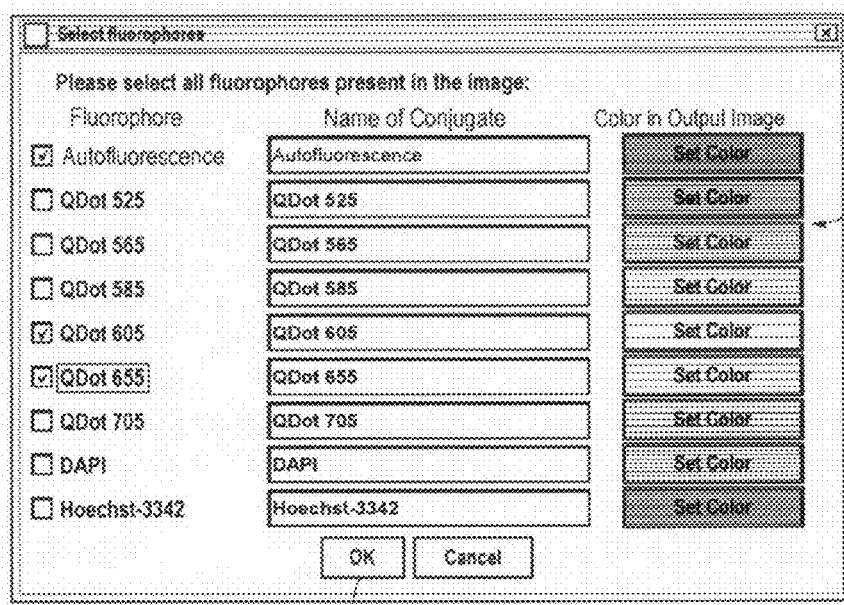
FIG. 8 is an illustration of a display presented on the workstation showing the user selecting the fluorophores which are present in the image, assigning an informative label to that fluorophore, and selecting a color to use to represent the individual fluorophores.

At step 110, the user is presented with a screen on the workstation by which they identify the fluorophores which were applied to the specimen, e.g., by checking a box or by means of selection from a drop-down list. An example is shown in FIG. 8. FIG. 8 shows a display 202 presented on the workstation display which shows a list 204 of quantum dots or other organic fluorophores, and the user checks the box next to the name of the fluorophore to indicate that it was applied to the specimen. The user checks the box next to autofluorescence to indicate that the user wishes to analyze the sample using a reference spectrum for autofluorescence appropriate for the tissue type being studied. Autofluorescence refers to naturally occurring fluorescence from molecules present in the sample. Analysis of the specimen to extract autofluorescence data makes use of a separate file containing autofluorescence spectra. The spectra in this file are computed by separately examining a sample that contains no external (added) fluorophores, and optimizing one or more reference spectra to optimally represent the spectral information collected from this sample. Subsequently, autofluorescence is treated in a manner identical to other fluorophores in the system, i.e., the fluorophores added to the specimen.

At step 112, the user selects the labels and colors to use for the individual fluorophores present in the specimen for display purposes. With reference to FIG. 8, the user is provided with a tool 206 on the display 202 by which the user can select a color for each of the fluorescence types present in the sample for use in display in an image of the specimen. For example, the user checks on the box "set color" next to the fluorophore and toggles through a sequence of colors to apply to the selected fluorophore. For example for autofluorescence the user can select blue, for the 605 nm quantum dot fluorophore "Qdot 605" the user can select red, and for the 655 quantum dot fluorophore "Qdot 655" the use can select a third color, e.g. yellow.

At step 114, with reference to FIGS. 2 and 4, the module 52 loads the image cube 70, and the list 72 of wavelengths and the list 74 of exposure times, described above in the context of FIG. 5.

At step 116, an optional exposure compensation operation is performed on the M images in order to normalize the response over the range of wavelengths. It is not unusual for different fluorophores to produce fluorescent signals of significantly different peak intensity. For example, "QDot 655" produces a much more intense signal than "QDot 525" when excited using the same light source, resulting in an image cube that is dominated by the "QDot 655" spectrum. To compensate for this situation and achieve optimal signals from both fluorophores, the auto-expose feature common on camera platforms can be used to automatically choose the duration for which the camera is exposed to the sample at each wavelength. This results in signal output levels that are similar across all wavelengths, but necessitates that a correction be applied during the quantitative analysis because the fluorescent signal intensity is a function of the exposure time, with longer exposure times resulting in higher signal intensity. One model that describes the dependence of signal intensity on exposure time is the linear model in which intensity scales linearly with respect to exposure time, as described in Y. Garini, A. Gil, I. Bar-Am, D. Cabib, and N. Katzir, *Signal to Noise Analysis of Multiple Color Fluorescence Imaging Microscopy*, Cytometry vol. 35 pp. 214-226 (1999). Pixels with an intensity signal equal to the maximum signal produced by the camera may not behave according to this model and should be either ignored or treated separately. The details of this treatment are discussed in the 'Constraints' portion of the Further examples and implementation details section.

At step 118, the process 52 performs additional image pre-processing functions, including subtraction of background signals (which may not be uniform across all the M images and which may be device-dependent), and application of other corrections for imperfections or noise in the spectral filters, the microscope or camera optics, variation in incident light output, and camera response. These details are not considered particularly pertinent and so a further discussion is omitted for the sake of brevity.

At step 120, the module 52 performs an interpolation of the fluorophore reference spectra (64 in FIG. 2) to the M sampled wavelengths in the image cube. This operation results in a matrix of illumination intensity at each wavelength, for each of the fluorophores, matrix I in equation (1) below. Each column in the matrix represents the spectral intensity value for one fluorophore, at the M wavelengths. Thus, each column has M rows. There are N columns in the matrix, one per fluorophore. The interpolation algorithm also corrects the reference spectra for exposure time, just like in the exposure compensation operation at step 116.

At step 122, the analysis module 52 performs a spectral unmixing process on the M images in the image cube. A variety of spectral unmixing processes are known in the art and considered to be suitable for this calculation. In one method, this spectral unmixing process multiplies a Moore-Penrose pseudo-inverse of the matrix I (indicated by $[I]^{-1}$ in equation (1)) by a vector of the total fluorescence intensity at each of the M wavelengths (vector S in equation (1)) to calculate a vector of concentration coefficients $C_1 \ldots C_N$. Methods for calculation of a Moore-Penrose pseudo inverse of an n×m matrix are known in the art. This operation is represented in equation (1) as follows:

$$\begin{bmatrix} c_1 \\ c_2 \\ \vdots \\ c_N \end{bmatrix} = \begin{bmatrix} I_1(\lambda_1) & I_2(\lambda_1) & \ldots & I_N(\lambda_1) \\ I_1(\lambda_2) & I_2(\lambda_2) & & \\ \vdots & & \ddots & \\ I_1(\lambda_M) & & & I_N(\lambda_M) \end{bmatrix}^{-1} \times \begin{bmatrix} S(\lambda_1) \\ S(\lambda_2) \\ \vdots \\ S(\lambda_M) \end{bmatrix} \quad (1)$$

This operation of equation 1 is performed for each pixel location, yielding a vector of coefficients $C_1 \ldots C_N$ for each pixel. The coefficients $C_1 \ldots C_N$ are related to the, concentrations of the 1 . . . N fluorophores present in the sample at each pixel location. The coefficients $C_1 \ldots C_N$ can be scaled to absolute concentrations, or considered representative of relative intensity, or relative concentration for the 1 . . . N fluorophores, e.g., on a scale of 0-255 in an 8-bit quantization of image intensities.

At step 124, the analysis module performs one or more morphological processing process to identify biological structures that may be present in the specimen, such as cells, cell membranes, nuclei, viruses, or other. Such processes basically identify the cells or other structures by identifying patterns and shapes present in an image of the specimen, e.g., closed curves of a certain size. The image upon which the morphological processing operates may one of the M images, a. composite of two or more of the M images, an image constructed from one or more of the coefficients $C_1 \ldots C_N$, a bright field image of the specimen, or other. In a preferred embodiment, the morphological processing is performed on an image constructed from the coefficients $C_1 \ldots C_N$. The morphological processing step was described previously.

At step 126, a quantitative analysis is performed for the biological structures, e.g., cells or nuclei, that are identified by the step 124. Such quantitative analysis was described previously.

At step 128, the resulting quantitative data is stored in the memory 38 of the workstation for use by the display module or process 54.

C. Display Module 54 (FIG. 2)

The operation of the display module will be described in conjunction with FIGS. 7 and 9-18. Basically, this module generates data for display of images of the specimen and quantitative data to the user on the display of the workstation. A variety of different tools and methods for display of quantitative data will be described.

Figure 7:
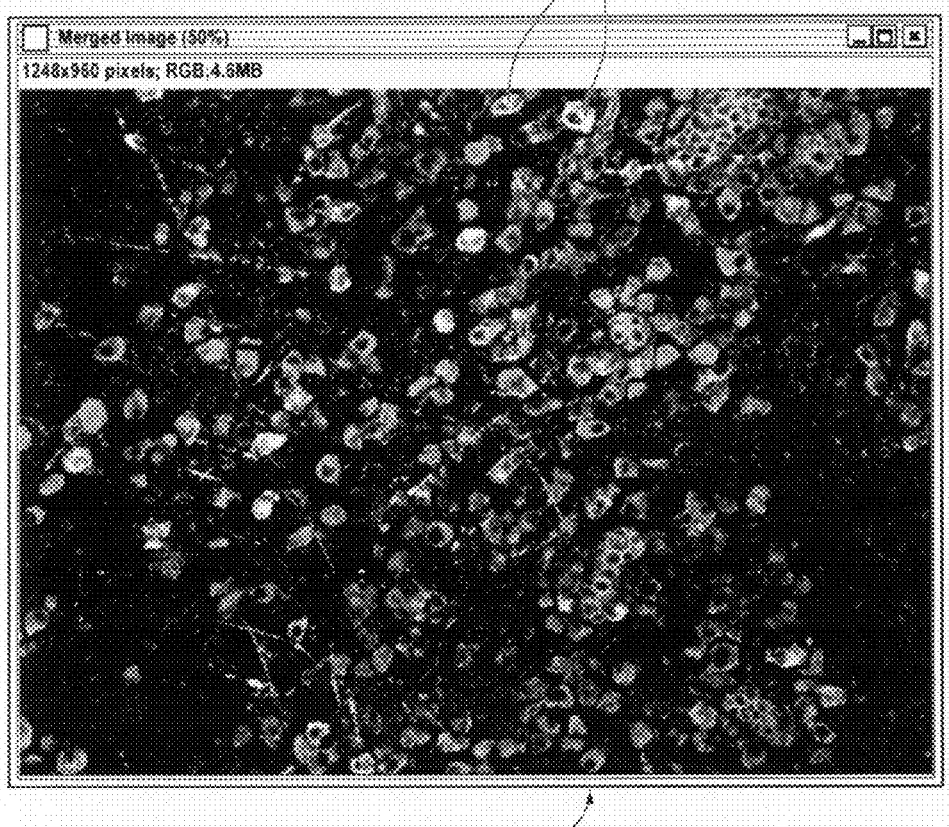
FIG. 7 is a typical image of the biological specimen in which the luminescent emission from multiple quantum dots contribute to the image and aid in highlighting cells or other cellular structures such as nuclei or cell membranes. The image of FIG. 7 can be generated from one or more the coefficients $C_1 \ldots C_N$.

FIG. 7 shows an image of the specimen which is displayed in a display 200 on the workstation. The image may be of the whole slide or a portion thereof. The image is typically multi-colored, with the fluorophore response from each of the fluorophores given a different color, as a result of the user interacting with the screen of FIG. 8. The image shown in FIG. 7 is preferably generated by the coefficients $C_1 \ldots C_N$ which were calculated in the spectral unmixing process.

Figure 9:
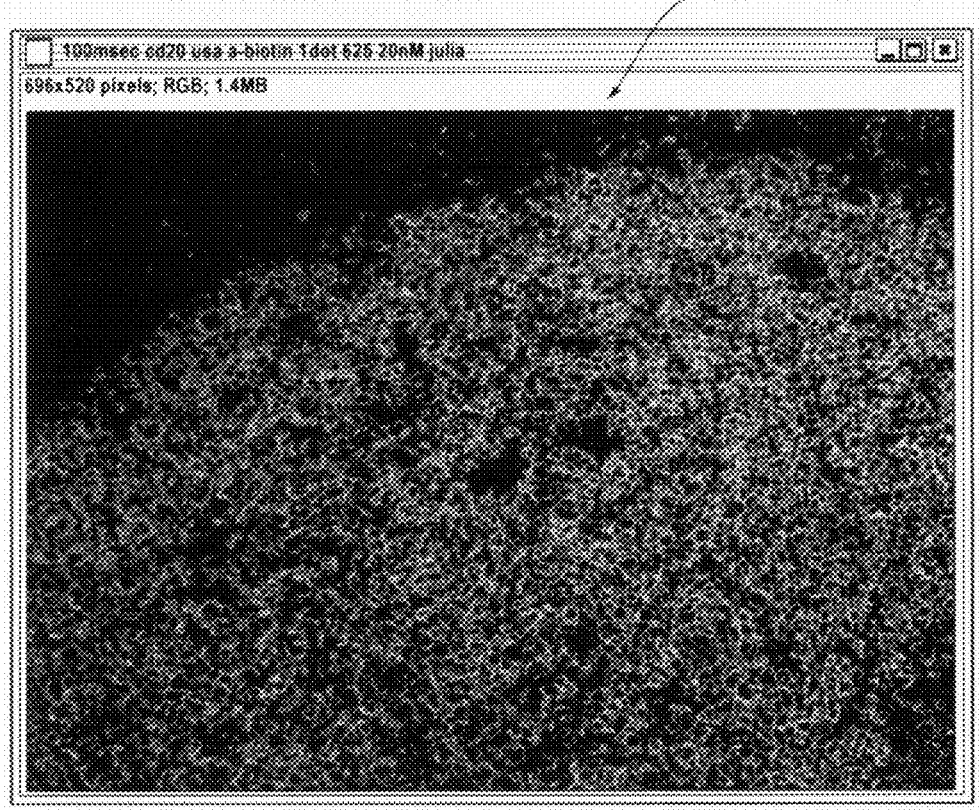
FIG. 9 is another image of the biological specimen, composed of two of the coefficients $C_1 \ldots C_N$.
Figure 10:
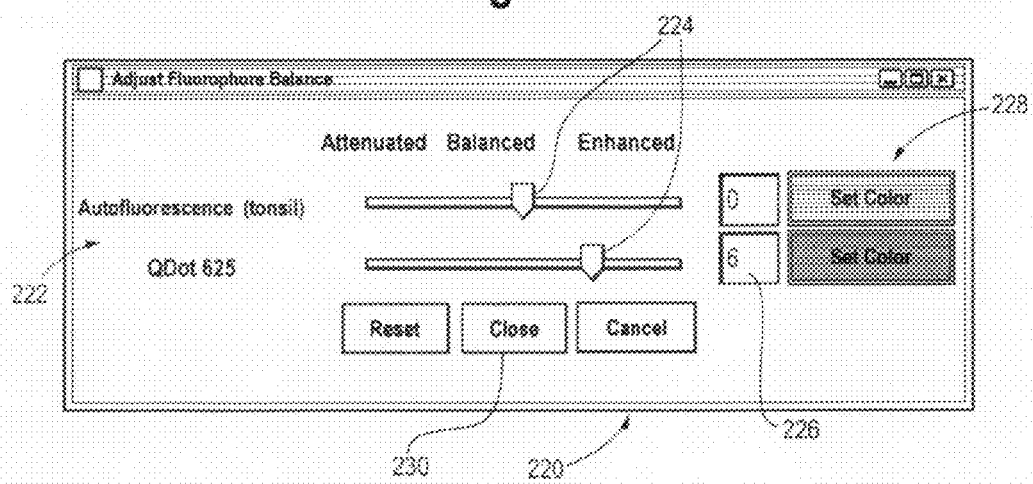
FIG. 10 is an illustration of a display presented on the workstation showing a feature by which a user can weight (i.e., enhance or attenuate) the contribution of one fluorophore or another in the generation of the image of FIG. 9. Note from FIG. 10 that one of the fluorophores may consist of autofluorescence from the specimen.

FIG. 9 is a second image of a specimen. The image 210 of FIG. 9 is generated from one of the coefficients $C_i$, along with autofluorescence signal. In this instance, the coefficient $C_i$ corresponds to a quantum dot conjugated to an antibody which binds to a protein on the surface of the cell membrane. Hence, in the image, the fluorescence signal due to coefficient $C_i$ appears as loops, corresponding to the shape of the cell membrane. The display process gives the user the opportunity to add in to the image the fluorescence signal from the other fluorophores which are present in the sample. When two fluorophores are present, one signal may be much stronger than the other. Therefore it is preferable to be able to adjust the fluorophore balance as an aid to visualization of the data. In FIG. 10, the user is presented with a display 220 with a portion 222 showing two fluorescence components in the sample, in this example autofluorescence and Qdot 625. The display includes a slider bar 224 by which the user can attenuate or enhance each of he fluorophores. For example, the user has enhanced the Qdot 625 signal by a scaling factor of 6, which is shown in the box 226. The user can also use the boxes 228 to reset the color of the fluorophores. When the user clicks on the Close button 230, the settings are saved and the image of both fluorophores with the new colors selection and weighting is displayed on the display of the workstation.

Recall from the previous discussion of FIG. 8 that the user assigns a color to each fluorophore for display purposes, and FIG. 10 shows that the user can later change that color. For instance, Qdot 525 might be assigned to yellow which in RGB space is (255,255,0)—i.e., the mixture of pure red and pure green. In general, fluorophore species i has color ($red_i$, $green_i$, $blue_i$). Once the source data image cube containing the overlapping spectra is separated into individual spectra (coefficients $C_1 \ldots C_N$), the intensity for each fluorophore at each pixel is known (on a scale of 0-255). To generate an image that shows multiple fluorophores mixed together, the colors are linearly mixed in RGB space. Other equivalent approaches are available for merging together, however linear mixing is used in this implementation. When displaying the image showing the contribution from all the fluorophores (an image constructed from all of the coefficients ($C_1 \ldots C_N$), the software takes the amount of red contributed from each fluorophore and computes the overall intensity- or concentration-weighted red value for each pixel. This is accomplished by taking the intensity of each fluorophore i (or in equation below "$intens_i$") times the red component of that fluorophore red; (or in the equation below "$red_i$"), summing this operation over all fluorophores.

$$\text{red} = \frac{\sum_i (\text{intens}_i * \text{red}_i)}{\sum_j \text{red}_j} \qquad (2)$$

A similar calculation is performed for the green and blue contributions.

The interface of FIG. 10 allows the user to artificially enhance one fluorophore over another, and achieves this by adding a multiplier in front of the intensity value. Thus, if the user wants to enhance fluorophore k by a factor of 2 (perhaps because it is being hidden by another, brighter fluorophore), the term in numerator of the above equation when i=k would be (2*$\text{intens}_k$*$\text{red}_k$). This multiplicative approach is simply one implementation of enhancement; other methods are possible.

FIG. 11 shows an example of a display of quantitative data for the specimen which is presented on the display of the workstation. The display 250 includes several histograms 252, 254 and 256, several scatter plots 260 and 262, and an image of the specimen 266. The histogram 252 show the size distribution of all cells in the specimen. The histogram 254 shows the distribution of cells showing positive autofluorescence signal, sorted by cell size. The histogram 256 shows the distribution of cells showing positive for Qdot 655, sorted by cell size. The scatter plot 260 plots points which indicate the relative intensity (or concentration) of one fluorophore as a function of the intensity (or concentration) of one of the other fluorophores, for cells or other biological structures which are positive for both fluorophores. For example, in the scatter plot 260, the plot shows the amount of Qdot 625 as a function of the amount of autofluorescence, which indicates that the cells producing relatively low autofluorescence signals also had relatively high signal from the Qdot 625 fluorophore (area 258).

The user is able to select any portion of the histograms 252, 254, 256 or scatter plots 260, 262 and conduct further quantitative analysis on the selected portion of the histogram. For example, the user has drawn a box 257 about a certain population of cells in the histogram C (plot 256). The box contains the larger cells in the histogram. The scatter plot 262 (plot E) shows the intensity of Qdot 625 signals as a function of the autofluorescence signal, for the sub-population of cells selected in box 257 in the histogram 256. The image 266 shows the specimen, with the selected cells 264 from the scatter plot 262 highlighted. For example, the larger cells indicated by the box 257 in the histogram are shown in a contrasting color (appearing as white in FIG. 11).

The display of FIG. 11 further includes additional statistical output data 270, such as data showing the intensity or concentration of each of the fluorophores for each of the biological structures, mean, median and standard deviation statistics, and so forth. The user scrolls down using the slider bars 274 and 272 to view all of the statistical data.

Figure 12:
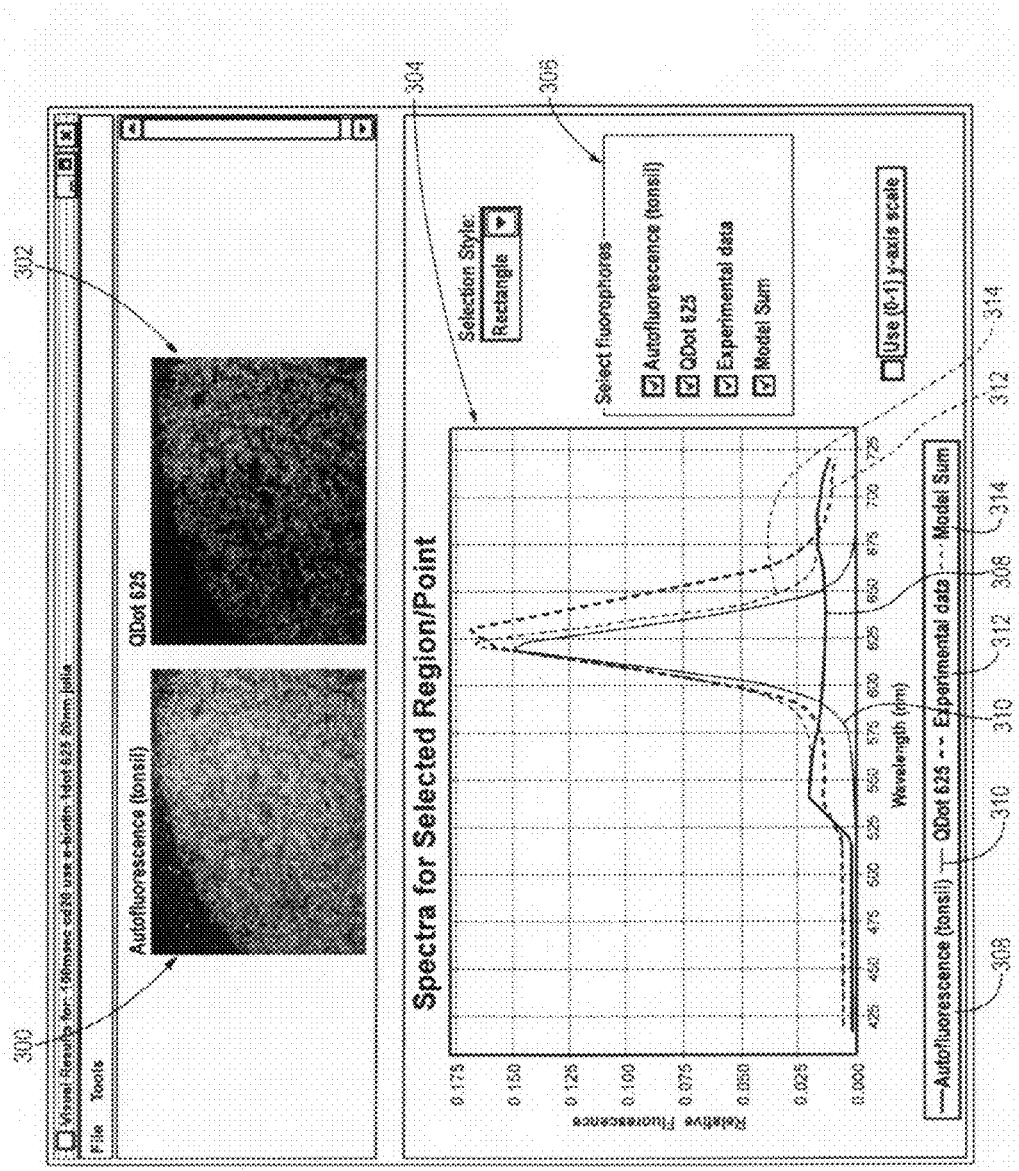
FIG. 12 is an illustration of a display on the workstation showing two separate images of the specimen, one from autofluorescence and another from a quantum dot emitting at 625 nm, and spectral data for a selected point or region in the images.

FIG. 12 shows another screen display presented on the workstation. The display includes two images 300 and 302, each of which shows the signal from one of the fluorophores present in the sample. In this example, image 300 shows the autofluorescence signal and the image 302 shows the Qdot 625 signal. The display also includes spectral data 304 for a portion of the image that is selected by the user. For example, the user can click on or select a point or region in the image 300 or 302, and the spectra data 304 shows the relative fluorescence data for autofluorescence, the 625 quantum dot, experimental data 312 and model sum 314. The model sum is the set of values $S_{model}(\lambda)$ from equation (3) computed based on the I matrix and computed coefficients $C_1 \ldots C_N$. The experimental data are the $S(\lambda)$ values that were used in equation (1) to compute the C coefficients. The region 306 allows the user to select which of the sets of data to present in the spectrum plot 304.

$$\begin{bmatrix} S_{model}(\lambda_1) \\ S_{model}(\lambda_2) \\ \vdots \\ S_{model}(\lambda_M) \end{bmatrix} = \begin{bmatrix} I_1(\lambda_1) & I_2(\lambda_1) & \ldots & I_N(\lambda_1) \\ I_1(\lambda_2) & I_2(\lambda_2) & & \\ \vdots & & \ddots & \\ I_1(\lambda_M) & & & I_N(\lambda_M) \end{bmatrix} \times \begin{bmatrix} C_1 \\ C_2 \\ \vdots \\ C_N \end{bmatrix} \qquad (3)$$

Figure 13:
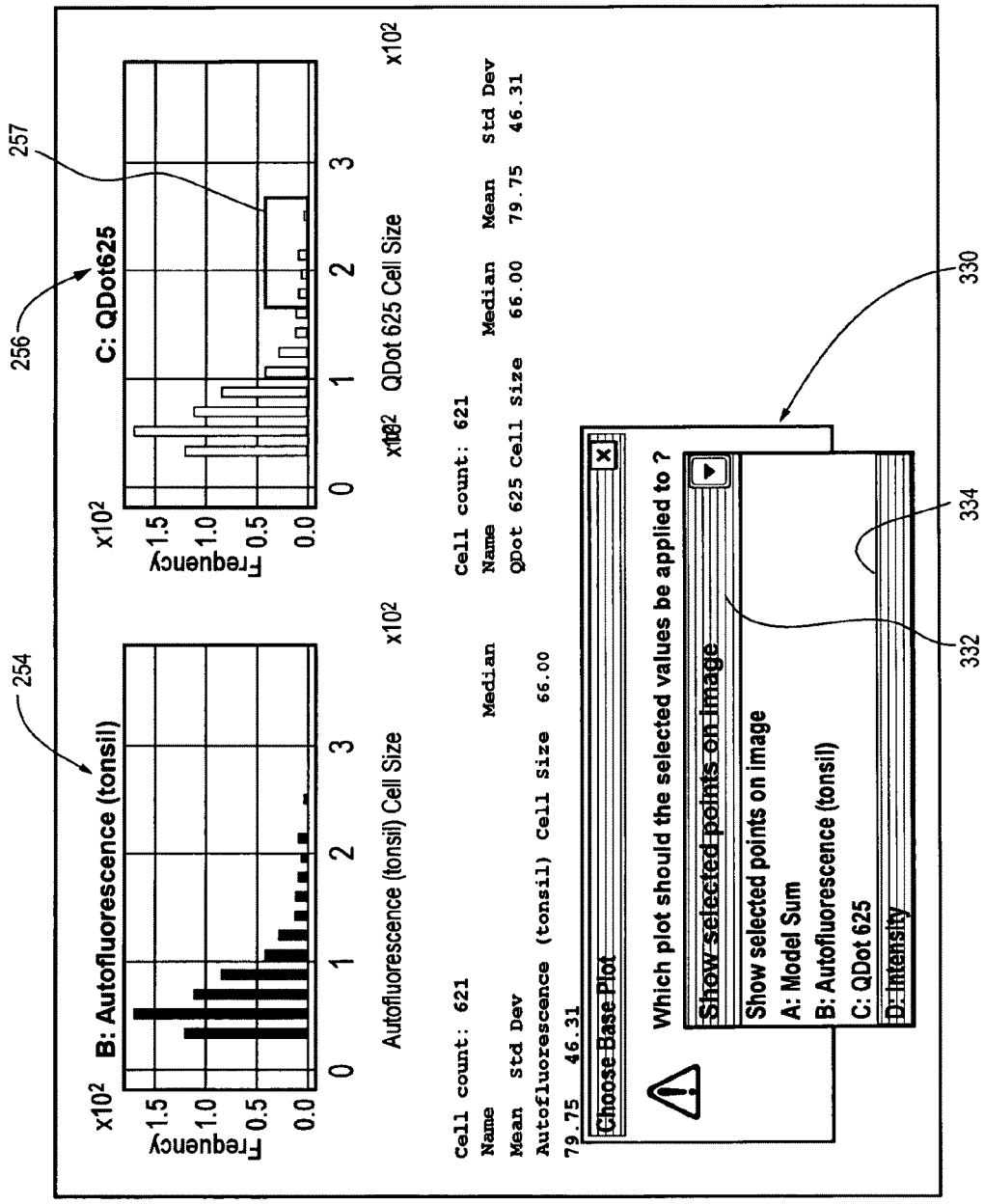
FIG. 13 is an illustration of two histograms showing quantitative data and showing a feature by which a user can select a sub-population of cells in one of the histograms and perform additional quantitative and qualitative analysis on the selected sub-population of cells.

FIG. 13 shows another example of the display of quantitative data. The display shows a histogram 254 showing the distribution of cell sizes for cells positive for autofluorescence, and a histogram 256 showing the distribution of cell sizes for cells positive for Qdot 625 signal. The display allows a user to select a region in the histogram 256 showing the cell size distribution for those cells that have a positive Qdot 625 signal. Here, the user has indicated the region by drawing the box 257 around a group of cells. This action pops up a dialog box 330 that asks the user what they would like to do with the selected points: show them highlighted on the image (332), or duplicate another of the plots showing only the cells that have been selected at 257. In FIG. 13, the user in indicating that they want to re-plot Plot-D from FIG. 11 (the intensity plot) with only the points selected in Plot-C (257 in FIG. 13) included. The result is shown in FIG. 14 as a new plot 340, with the scatter plot showing the data points 342 corresponding to the subpopulation of cells from 257, showing Qdot 625 intensity as a function of autofluorescence for cells having a non-zero response to both fluorescence signals.

Figure 15:
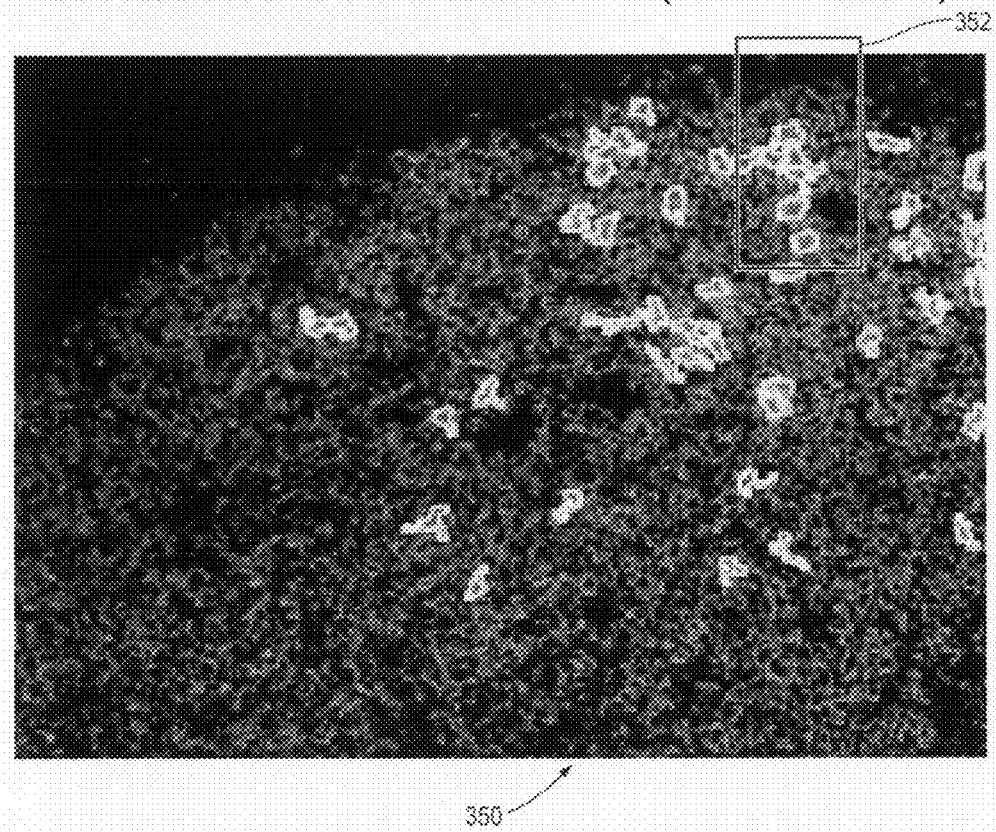
FIG. 15 is an illustration of a display presented on the workstation showing an image of the specimen and a feature by which a user can select a discrete sub-region of the image and have additional quantitative analysis performed on the selected sub-region.

Next, the points which were selected are shown as highlighted cells on a merged image 350 as shown in FIG. 15. The cellular objects shown in white in FIG. 15 are the cells selected in the histogram 256 by the box 257 (FIG. 14). The image of FIG. 15 is constructed from the autofluorescence signal and the coefficient $C_i$ corresponding to the 625 nm quantum dot.

Additionally, the user can note where the interesting cells are on the merged image of FIG. 15, by drawing a region of interest (ROI) 352 on the merged image window with the mouse. The user is able to inspect spectral information or other quantitative data for that region 352 in a visual results window, shown in FIG. 16. When you select a region on an image as shown in FIG. 15, the curves in the plot on the bottom of the visual results window (FIG. 16) are updated. This technique may take advantage of data linking and data brushing, described in further detail below.

Figure 16:
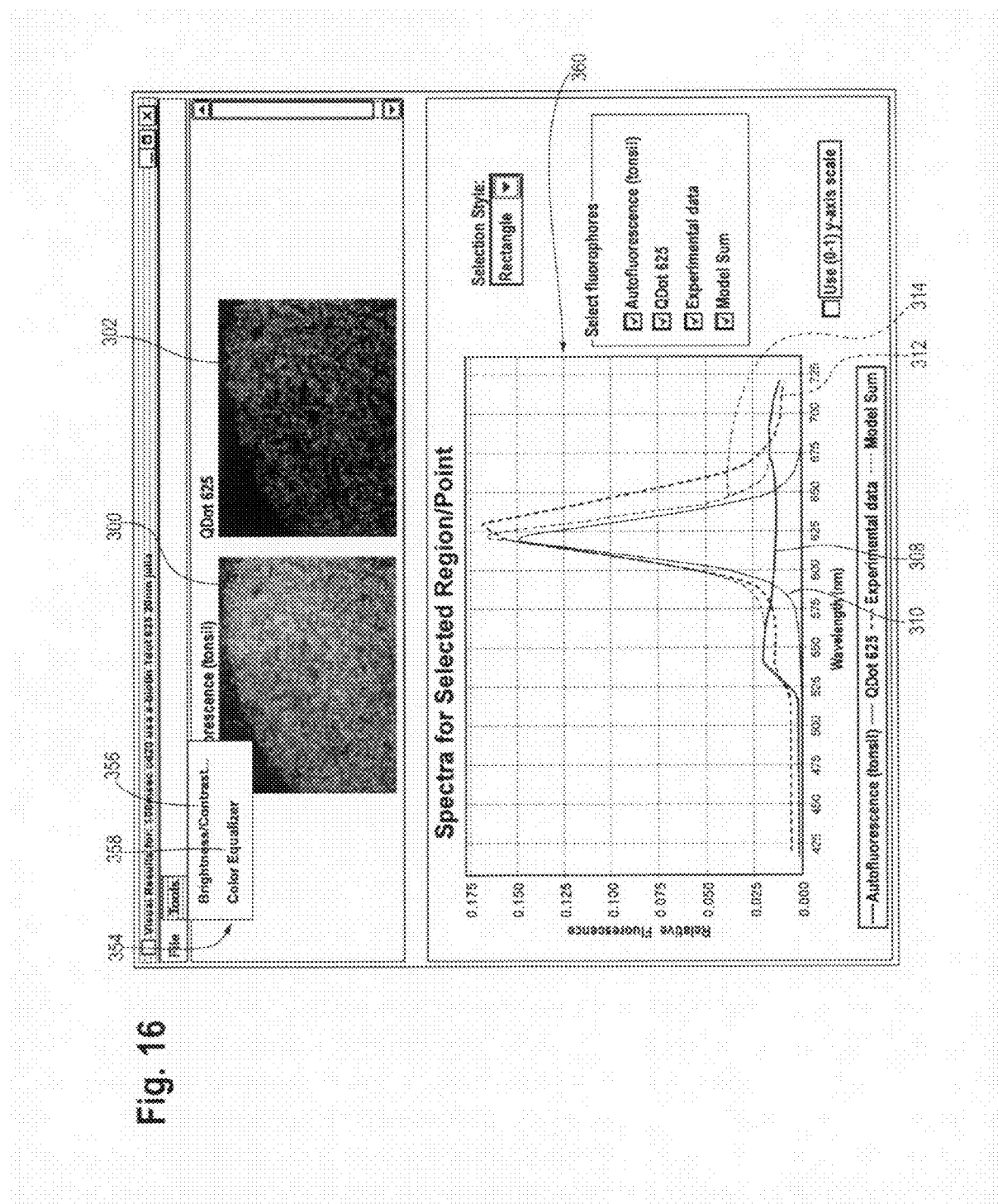
FIG. 16 is an illustration of a display presented on the workstation showing two images of the same portion of the specimen, one showing the autofluorescence and the other the luminance from a 625 nm quantum dot, and spectra for the region of the specimen selected in the procedure shown in FIG. 15.

FIG. 16 shows an example of an image 350 having two components from two different fluorophores. In this example there is autofluorescence image 300 and the 625 nm Qdot image 302.

The tools menu is expanded in FIG. 16 to show the suboptions. Brightness/Contrast 356 launches a tool that allows the user to vary these quantities in the merged image, and Color Equalizer launches the tool shown in FIG. 10 and described previously to allow the user to enhance one or more fluorophores for display purposes only. FIG. 16 also shows another example of the spectra in the region 352 selected in FIG. 15, including the autofluorescence spectrum 308, the 625 quantum dot spectrum 310, the experimental data 312 and the model sum 314.

Figure 17:
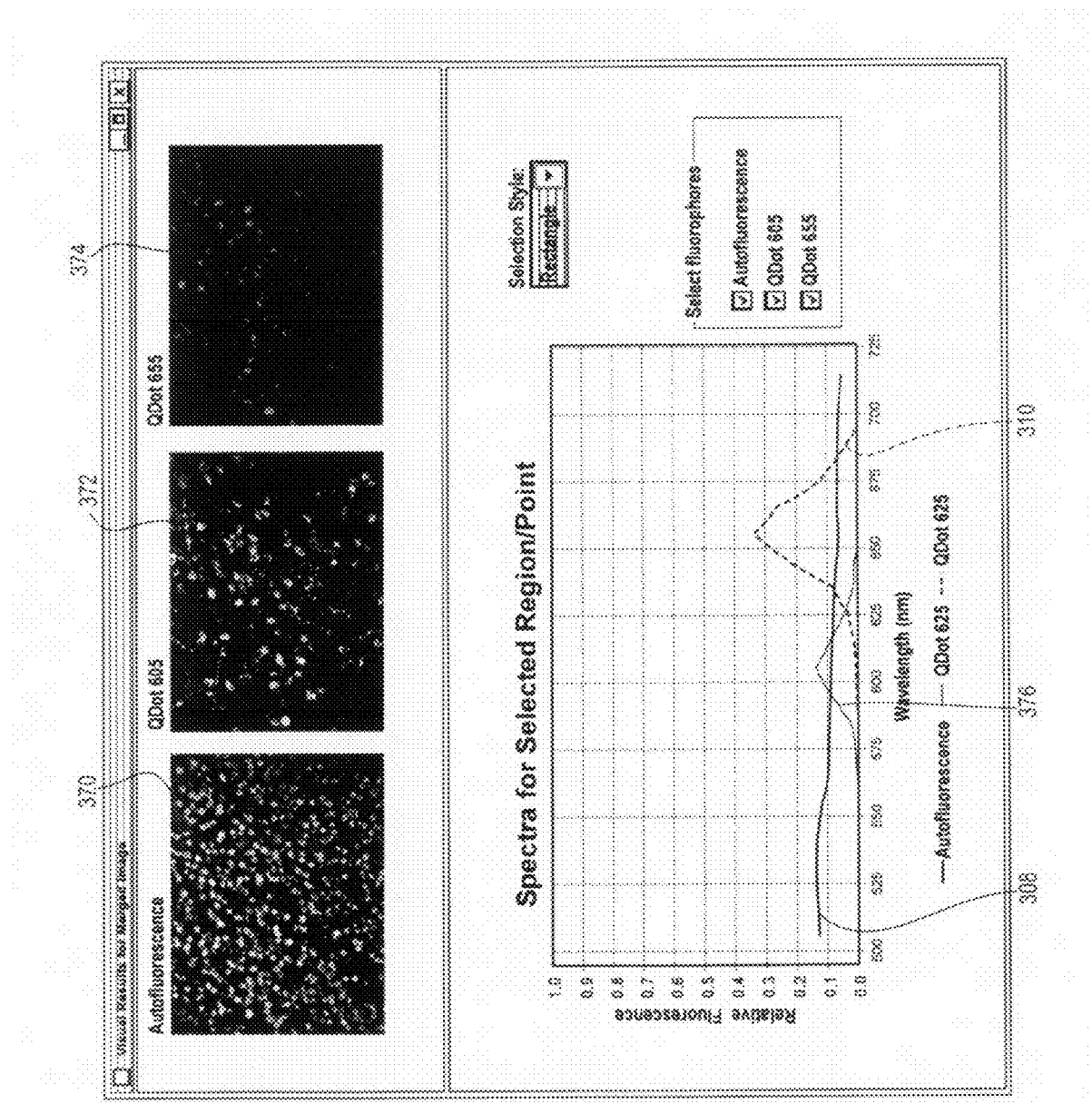
FIG. 17 is an illustration of a display presented on the workstation showing three images of the same region of the specimen, one image showing the autofluorescence signal from the specimen, one showing the signal from a 605 nm quantum dot, and one showing the signal from a 655 nm quantum dot.

FIG. 17 shows another example of the display of images from the specimen. In the example of FIG. 17, there are three images, namely an autofluorescence image 370, a 605 quantum dot image constructed from the coefficient $C_i$ for the 605 fluorophore, and a 625 quantum dot image constructed from the coefficient $C_j$ for the 625 fluorophore. The spectra 308, 376 and 310 for the fluorophores are shown in the plot below the images. The images 370, 372 and 374 can be images of the entire specimen, or images of only a portion of the specimen, e.g., a sub-region selected by the user as shown in FIG. 15.

FIG. 18 is another example of a display 400 showing a combination of scatter plots, histograms, image, and statistical data for a specimen. The scatter plot 402 plots intensity of the 605 nm Qdot as a function of autofluorescence for cells having a positive signal for both types of fluorescence. The autofluorescence and 605 Qdot values are plotted on a scale of 0 to 255 for convenience, and the scatter plot 402 is zoomed in to magnify the region containing data. The units for the X and Y axis of the scatter plots can be scaled to absolute concentration values using appropriate scaling factors.

Similarly, the scatter plot 410 shows the distribution of the Qdot 655 values as a function of the Qdot 605 values, for cells positive for both fluorophores. The scaling factors on the X and Y axes 412 and 414 could be relative intensity or concentration or absolute intensity or concentration.

The statistical output 422 presents statistical data for all of the identified objects in the specimen, including the area or size of the objects, and the intensity values for each object. Additional statistics on the objects, such as mean, median and standard deviation values can be presented as well.

Further Examples and Implementation Details

Z-Stack Imaging

Optical sectioning is the technique of optically imaging "slices" of a three-dimensional sample by changing the focal plane in the vertical direction and taking images at each plane. See D. A. Agard, "*Optical Sectioning Microscopy: Cellular Architecture in Three Dimensions,*" Annual Reviews in Biophysics and Bioengineering, vol. 13, pp. 191-219, 1984. S. Joshi and M. I. Miller, "*Maximum a Posteriori Estimate with Good's Roughness for Three-Dimensional Optical-Sectioning Microscopy,*" Journal of Optical Society of America, vol. 10, no. 5, pp. 1078-1085, 1993.

The camera of FIG. 1 can use this technique to operate at multiple depths of field (i.e., focus settings in the Z direction, into the tissue sample), and at each depth of field the M images are obtained. The resulting data set includes an image cube at each depth. From this data set, three dimensional quantitative data from the specimen is obtained. When the user is presented with the quantitative data, the user is given an option to select the depth of field they wish to view and analyze. Additional, quantitative data is obtained for a three dimensional volume of the tissue section. Such quantitative data is presented to the user.

The separate 2-dimensional images can be registered mathematically into a 3-dimensional representation of the cells and tissues. One additional application of optical sectioning is to improve resolution of the 2-dimensional images. See *Enhanced Resolution from Three-dimensional Imaging*: W. A. Carrington, R. M. Lynch, E. D. Moore, G. Isenberg, K. E. Fogarty, and F. S. Fay, "*Superresolution Three-Dimensional Images of Fluorescence in Cells with minimal Light Exposure,*" Science, vol. 268, pp. 1483-1487, Jun. 9, 1995. The concepts of data linking/brushing have been extended to 3-dimensional representations. See Pak Chung Wong, R. D. Bergeron, "*Brushing techniques for exploring volume datasets,*" vis, p. 429, Eighth IEEE Visualization 1997 (VIS'97), 1997. This invention further extends them to include 3-dimension spectral images in the domain of fluorescence and concentration.

Constraints

The image analysis software uses constraint algorithms to handle errors in the data. For example, assume that quantitative analysis module is analyzing a pixel for presence of fluorophores X, Y, and Z. If the module encounters a pixel that has a negative value Y (a non-physical situation), the module re-analyzes that pixel for fluorophores X & Z only, and uses the new results for X and Z, and sets Y to zero. Also, if any fluorophore results in a concentration that exceeds the maximum that can be detected by the camera, the algorithm sets it to the maximum allowable value. Other approaches to handling anomalous results, such as omitting such pixels from the analysis, are possible, and the algorithm described above is one possible embodiment.

Data-Linking/Brushing

Multidimensional data linking and data brushing are well-accepted means for interacting with high-dimensional data. See *Interactive Data Exploration with Multiple Views (Data Linking and Data Brushing)*: Sigmar-Olaf Tergan (Editor), Tanja Keller (Editor), *Knowledge and Information Visualization: Searching for Synergies* (Lecture Notes in Computer Science) Springer-Verlag, Berlin, 1998. The analysis module of this disclosure extends the concepts of data linking and data brushing to the case where one view of the data is in the form of images of cells in culture or tissue. The image can be either a rendering of the raw fluorescence, or a synthetic image, e.g. images generated from the concentration coefficients as explained above.

Intelligent Whole Slide Imaging

In systems used in current practice, imaging of biological specimens is typically performed on multiple samples arranged on a slide. Tissue microarrays, for example, are paraffin blocks containing as many as 1000 tissue samples arranged on a slide in a rectangular fashion. Slides are prepared, using manual operations or automated devices, by taking thin slices of the paraffin material and mounting each slice on a slide. See Battifora, H. *The multitumor (sausage) tissue block: novel method for immunohistochemical antibody testing*. Lab Invest 1986, 55:244-248; Battifora, H. et al., *The checkerboard tissue block. An improved multitissue control block*. Lab Invest 1998, 63:722-724; Kononen J, et al., *Tissue microarrays for high-throughput molecular profiling of tumor specimens*. Nat Med 1998, 4:844-847.

Image acquisition is typically done interactively. The pathologist or technician images a whole slide at low resolution and selects regions containing tissue samples to view at higher resolution. The selected regions of interest are then imaged at a higher resolution (magnification), for example if the pathologist wishes to record images containing specific cell types (classified by e.g. tissue type or normal vs. cancer) at high resolution for later processing or review by a specialist.

In this approach, only small, manually-selected regions are imaged at high resolution, and detailed analyses of specific regions of interest are typically done at a later time. Because of the large number of samples on a slide, and because this process is user intensive and time-consuming, some samples may not be imaged at the same time, and the sample may have degraded during the delay. Further, the experience and ability of the pathologist or researcher may affect which regions are selected, resulting in irreproducible and possibly erroneous results.

One solution to these problems is to record a single image at high resolution. For example, DMetrix, Inc. has developed a scanning system utilizing an array of microscopes and cameras (see e.g. U.S. Patent application publication 2004/0101210 "Miniaturized microscope array digital slide scanner"). This approach suffers from two drawbacks. The first is that the data storage requirements for whole slide imaging at high resolution are prohibitive for many applications. For example, the DMetrix system records a single 12 gigabit grayscale image. While this technique could be used with the methods of this invention, if 100 or more images were to be collected at different wavelengths, it would result in an image cube of 1.2 terabytes or more for a single slide, and hundreds of terabytes for the three-dimensional (Z-stack, multiple depth of field) imaging applications mentioned elsewhere in this document. The second drawback with the existing approach is that standard cameras cannot take high resolution images of a whole slide at once because they lack sufficient field of view and the imaging arrays in the cameras are not large enough.

One method of approaching the goal of an intelligent approach to whole slide imaging is to generate a low resolution image of the entire slide (or possibly a low resolution image cube of the entire slide) and then use the automated image segmentation and classification features of the morphological processing processes to identify important regions on a slide (e.g., biological structures with a high signal for one or more fluorophores) and then collect, preferably automatically, a high-resolution image cube of only these important regions on a slide. In one embodiment, the high resolution image cube of the important regions of the slide is collected shortly after the low resolution image is obtained, e.g., a few minutes later, after the morphological processing steps have been performed and the important areas of the slide identified. However, quantum dot fluorophores are less subject to degradation then organic fluorophores and in some embodiments the high resolution image cube can be obtained later on.

The procedure followed in this automated approach includes the following steps.

1) Acquire one or more low-resolution images, or alternatively an image cube, of the entire slide.
2) Using automated image segmentation and classification algorithms (i.e., morphological processing processes as described above), areas of the slide which contain regions of interest such as tissue spots are identified from the one or more low resolution image, the image cube or an image derived from the image cube (e.g., an image constructed from concentration coefficients). Such locations are flagged. The locations of such tissue spots could be either referenced to pixel locations in the low resolution image or XY coordinates of the motion stage that moves the slide relative to the camera and microscope optics during acquisition of the low resolution image.
3) Acquire higher resolution images of the tissue spots at multiple wavelengths, basically acquiring an image cube of the important areas of the slide. The location coordinates from step 2) are used to position the correct portions of the slide in the field of view of the camera microscope. The microscope has a higher magnification objective lens in place for higher resolution imaging. While the higher resolution image of the tissue spots are obtained, the camera system records at the same time metadata summarizing each image, e.g. a slide identifier, a tissue sample identifier, image magnification and the image location (or slide location).
4) If camera limitations, storage requirements or other constraints prevent high resolution acquisition of entire tissue spots, the morphological processing further processes the tissue spots to identify smaller regions of interest within the tissue spots using automated image segmentation and classification algorithms. Such smaller regions of interest could be regions containing cells, cellular components, genes, DNA fragments, messenger RNA entities, viruses, or whatever other structures are of interest in the given assay. Alternatively, such smaller regions could be only those regions where one or more fluorophore signal is present.
5) Acquire and record high-resolution spectral images (image cubes) for each region of interest.

The coefficients $C_1 \ldots C_N$ are calculated for each pixel imaging the one or more regions of interest or tissue spots in the high resolution image cube. A quantitative analysis of the regions of interest or tissue spots is performed as explained previously, including calculating fluorophore concentrations for biological structures in the tissue spots or regions of interest from the coefficients $C_1 \ldots C_N$ The quantitative analysis of the regions or interest or tissue spots proceeds as described above. The display of the results of the quantitative analysis results and images of the regions of interest and tissue spots proceeds using the examples described previously.

The process of automated selection of regions of interest (steps 3-5) can be repeated an arbitrary number of times, with multiple intermediate resolutions sampled before the reaching the required resolution. This requires that the image analysis software system have control of the field of view and magnification of the microscope, and control of the digital camera as well. Many commercially available setups provide programming interfaces that permit this type of software control of the microscope and camera. This approach provides for completely automated analysis of a whole slide, as well as automated imaging of a whole slide for later interactive viewing and data exploration.

A similar approach can be used for other types of supports for biological specimens besides slides, such as, for example, multiwell plates containing cultured cells.

Equivalent Imaging Methods

The data representing the image cube (pixel signal level for rows, columns and at M different wavelengths) can be obtained in a variety of different orders. For example, we have described generating a two-dimensional image of the specimen at M wavelengths. Alternatively, one could use a camera such as shown in U.S. Pat. No. 5,926,283 which captures data at multiple wavelengths for one row/column of an image and then collects the data for the other rows/columns. The end result is still a cube having rows/columns/wavelengths, with the information having been collected and/or stored in a different order.

As another example, the images making up the image cube could be captured with a so-called line-scan type digital imager in which the pixels of the camera are arranged in a 1×N linear array of pixels. In this type of imager, a row of image data is obtained and then relative movement between the imager and the slide occurs, then a second row of image data is obtained, and so forth, until the entire slide is imaged. To obtain the image cube, rows of image data obtained at one wavelength are obtained sequentially to image the two-dimensional entire specimen or slide at the first wavelength. Then, a different spectral filter is placed in front of the camera and rows of image data are obtained sequentially at a second wavelength. A different filter is placed in front of the camera and rows of image data are obtained sequentially at a third wavelength. The process continues until images of the slide at all the M wavelengths have been obtained.

Software Product for Generic Workstations

The software described above, including the initialization and set-up module, analysis module, and the display module, can be loaded on a disk or other machine readable medium and provided as a stand alone product for commercially available workstations in order to upgrade the workstation to function as described herein.

In one embodiment, the instructions include a set of instructions for: (a) determining from a set of M images the coefficients $C_1 \ldots C_N$ for each pixel described above; (b) morphologically processing an image of the specimen to identify cells or cellular components in the specimen, (c) conducting a quantitative analysis of the specimen including calculating quantum dot concentrations for the cells or cellular components identified in step (b) from the coefficients $C_1 \ldots C_N$; and (d) generating data for display of the results of the quantitative analysis process (c) on a display associated with the processing unit.

Additionally, the software including the initialization and set-up module, analysis module, and the display module, can be loaded on a network server and executed by a processing unit in the network server. In this case, the user interacts with the software via a client application running on separate computing platform, e.g., a personal computer or workstation, which is coupled to the network that includes the network server. For example, the software may include a Web interface to allow a remote client to access and view displays of the quantitative data and images of the specimen, and interact with it as described above, but the software processes for calculation the coefficients, morphologically processing an image of the specimen, conducting the quantitative analysis and generating display data are executed in the network server.

Quantum Dots

As used in the claims the term "quantum dot" is intended to be read broadly to cover luminescent semi-conductor nanocrystals generally, including CdSe nanoparticles as well as CdTe or other luminescent semi-conductor nanoparticles. Such particles may take any geometric form, including spherical, rod, wires, or other. Gold particles may also be used.

All references and literature cited above are specifically incorporated by reference herein.

While a number of exemplary aspects and embodiments have been discussed above, those of skill in the art will recognize certain modifications, permutations, additions and sub-combinations thereof as being present in the disclosure. It is therefore intended that the following appended claims and claims hereafter introduced are interpreted to include all such modifications, permutations, additions and sub-combinations as are within their true spirit and scope.

We claim:

1. A method for analysis of a biological specimen in which between 1 ... N quantum dots are applied to the specimen, comprising the steps of:
    (a) collecting an image cube of the specimen comprising image data for a multitude of pixels at M different wavelengths, where M is an integer greater than 2;
    (b) determining from the image cube coefficients $C_1 \ldots C_N$ for each pixel, wherein the coefficients $C_1 \ldots C_N$ are related to the concentrations of the 1 ... N quantum dots present in the specimen imaged by each pixel;
    (c) morphologically processing an image constructed from the coefficients $C_1 \ldots C_N$ to identify cells or cellular components in the specimen,
    (d) conducting a quantitative analysis of the specimen including calculating fluorophore concentrations for the cells or cellular components identified in step (c) from the coefficients $C_1 \ldots C_N$; and
    (e) displaying the results of the quantitative analysis process (d) on a display of a workstation.

2. The method of claim 1, wherein M is an integer greater than 10.

3. The method of claim 1, wherein M is an integer greater than 20.

4. The method of claim 1, wherein the morphological processing step measures the size of the cells or cellular components and counts the number of cells or cellular components identified in the specimen.

5. The method of claim 1, wherein step (e) further comprises the step of providing a feature allowing a user to select a segment of an image of the specimen, and providing a graph of spectral data for the segment of the image selected by the user.

6. The method of claim 1, wherein between 2 and N quantum dots are applied to the specimen and wherein the display step (e) includes steps of displaying:
    i) an image of the specimen constructed from one or more of the coefficients $C_1 \ldots C_N$ at each pixel;
    ii) a histogram of cells or cellular components identified from the specimen sorted by size for at least at least one of the 2 ... N quantum dots applied to the sample; and
    iii) one or more scatter plots of concentration of one of the 2 ... N quantum dots as a function of concentration of one of the other 2 ... N quantum dots for biological structures identified in the specimen having a positive signal for the quantum dots presented in the scatter plot.

7. The method of claim 1, wherein the display step (e) includes a step of displaying quantitative analysis results as either a histogram of a fluorophore concentration as a function of identified biological structures, a scatter plot of a first fluorophore intensity as a function of a second fluorophore intensity for biological structures having a positive signal for the first and second fluorophores, or both, and wherein the display process further includes a feature by which a user may select a portion of the scatter plot or the histogram and conduct further quantitative analysis on the portions of the specimen corresponding to the selected portion of the scatter plot or histogram.

8. The method of claim 1, wherein the image cube comprises M images, and wherein the method further comprises a step of performing an adjustment of the M images to normalize the response of the quantum dots to the light conditions when the M images were generated.

9. The method of claim 1, wherein in step (e) the results of the quantitative analysis process (d) are presented as a histogram of the number of cells or cellular components sorted by size, for one or more of the 1 ... N quantum dots applied to the sample.

10. The method of claim 9, wherein the method further comprises the step of providing a feature allowing a user to select a portion of a histogram, scatter plot or other visualization of the quantitative data and responsively displays an image of the specimen with the biological structures associated with the selected portion of the histogram, scatter plot or other visualization presented in the image.

11. The method of claim 9, wherein step (e) further comprises a step of providing a facility by which a user may select a portion of the histogram and an image is presented showing biological structures corresponding to the selected portion of the histogram.

12. The method of claim 1, wherein step (e) further comprises the step of providing a feature allowing a user to select a segment of an image of the specimen and displaying quantitative results for the selected segment of the image.

13. The method of claim 12, step (e) further comprises a step of presenting an image of the specimen wherein the image constructed from one or more of the coefficients $C_1 \ldots C_N$ for each pixel.

14. The method of claim 1, further comprising the step of generating a plurality of images of the specimen at a plurality of discrete wavelengths at a plurality of depths of field.

15. The method of claim 14, further comprising the step of using the images generated at the plurality of depths of field to enhance the resolution of the images of the specimen.

16. The method of claim 1, further comprising a step of interpolating spectral data associated with the 1 . . . N quantum dots to the M wavelengths at which the specimen was imaged and using the interpolated spectral data to determine the coefficients $C_1 \ldots C_N$ for each pixel.

17. The method of claim 16, wherein the coefficients $C_1 \ldots C_N$ are determined with reference to reference spectral data, and wherein the method further comprises the step of performing an exposure compensation operation wherein the duration in which a camera is exposed at each of the M different wavelengths to produce the image data is adjusted to compensate for different quantum dots producing different intensity signals.

18. The method of claim 1, wherein the quantitative results comprise a plot of concentration of one quantum dot as a function of concentration of a second quantum dot for biological structures identified in the specimen having a positive signal for both quantum dots.

19. The method of claim 18, wherein the coefficients $C_1 \ldots C_N$ are scaled to absolute concentrations of the quantum dots in the sample and wherein the plots of concentration are expressed in terms of absolute concentrations.

20. The method of claim 18, wherein step (e) further comprises a step of providing a facility by which a user may select a portion of the plot and an image is presented showing biological structures corresponding to the selected portion of the plot.

21. The method of claim 1, wherein step (e) further comprises the steps of presenting an image of the specimen on the display, and providing a tool by which color intensity for a selected quantum dot can be selectively weighted by the user to thereby change the appearance of the image of the specimen on the display.

22. The method of claim 21, wherein the display process further provides a tool by which the user can select a color for display of the 1 . . . N quantum dots.

23. The method of claim 22, wherein between 2 and N quantum dots are applied to the specimen and wherein the display step (e) displays the quantitative results as one or more scatter plots of concentration of one of the 2 . . . N quantum dots as a function of concentration of one of the other 2 . . . N quantum dots for biological structures in the specimen which test positive for both of the quantum dots presented in the one or more scatter plots.

* * * * *